(12) United States Patent
Gallop et al.

(10) Patent No.: US 7,560,483 B2
(45) Date of Patent: Jul. 14, 2009

(54) METHODS FOR SYNTHESIS OF PRODRUGS FROM 1-ACYL-ALKYL DERIVATIVES AND COMPOSITIONS THEREOF

(75) Inventors: Mark A. Gallop, Los Altos, CA (US); Jia-Ning Xiang, Palo Alto, CA (US); Fenmei Yao, Mountain View, CA (US); Laxminarayan Bhat, Santa Clara, CA (US); Cindy X. Zhou, Palo Alto, CA (US)

(73) Assignee: XenoPort, Inc., Santa Clara, CA (US)

( * ) Notice: Subject to any disclaimer, the term of this patent is extended or adjusted under 35 U.S.C. 154(b) by 501 days.

(21) Appl. No.: 11/158,405

(22) Filed: Jun. 21, 2005

(65) Prior Publication Data

US 2005/0239725 A1  Oct. 27, 2005

Related U.S. Application Data

(63) Continuation of application No. 10/167,797, filed on Jun. 11, 2002, now Pat. No. 6,927,036.

(60) Provisional application No. 60/358,603, filed on Feb. 19, 2002, provisional application No. 60/371,535, filed on Apr. 9, 2002.

(51) Int. Cl.
| | |
|---|---|
| C07C 271/22 | (2006.01) |
| A61K 31/27 | (2006.01) |
| C07D 403/04 | (2006.01) |
| A61K 31/497 | (2006.01) |
| C07C 235/50 | (2006.01) |
| A61K 31/166 | (2006.01) |
| C07C 271/06 | (2006.01) |
| C07C 271/08 | (2006.01) |
| C07C 271/10 | (2006.01) |
| C07C 271/12 | (2006.01) |
| C07C 271/14 | (2006.01) |
| C07C 271/16 | (2006.01) |
| C07C 271/18 | (2006.01) |
| C07C 271/20 | (2006.01) |
| C07C 271/24 | (2006.01) |
| C07C 271/26 | (2006.01) |
| C07C 271/28 | (2006.01) |
| C07C 271/30 | (2006.01) |
| C07D 401/04 | (2006.01) |
| C07D 475/08 | (2006.01) |
| A61K 31/5355 | (2006.01) |
| A61K 31/4985 | (2006.01) |
| C07D 401/08 | (2006.01) |
| C07D 241/04 | (2006.01) |
| C07H 15/234 | (2006.01) |
| A61K 31/7036 | (2006.01) |
| C07H 15/236 | (2006.01) |
| A61K 31/704 | (2006.01) |
| C07H 15/24 | (2006.01) |
| C07D 235/28 | (2006.01) |
| A61K 31/4168 | (2006.01) |
| A61K 31/427 | (2006.01) |
| C07D 277/82 | (2006.01) |
| A61K 31/428 | (2006.01) |
| C07D 235/22 | (2006.01) |
| C07D 263/28 | (2006.01) |
| A61K 31/421 | (2006.01) |
| C07D 209/32 | (2006.01) |
| A61K 31/4045 | (2006.01) |
| C07D 209/08 | (2006.01) |
| A61K 31/4192 | (2006.01) |
| C07D 233/42 | (2006.01) |
| A61K 31/4178 | (2006.01) |
| C07D 235/32 | (2006.01) |
| C07D 403/12 | (2006.01) |
| A61K 31/4164 | (2006.01) |
| C07D 233/50 | (2006.01) |
| A61K 31/341 | (2006.01) |
| C07D 307/36 | (2006.01) |
| C07D 233/06 | (2006.01) |
| C07D 277/42 | (2006.01) |
| C07D 277/38 | (2006.01) |
| A61K 31/426 | (2006.01) |
| C07D 209/52 | (2006.01) |
| A61K 31/4025 | (2006.01) |
| A61K 31/4375 | (2006.01) |
| C07D 211/82 | (2006.01) |
| A61K 31/4418 | (2006.01) |
| C07D 213/65 | (2006.01) |
| A61K 31/4412 | (2006.01) |
| C07D 211/14 | (2006.01) |
| A61K 31/4458 | (2006.01) |
| C07D 211/42 | (2006.01) |
| A61K 31/45 | (2006.01) |
| A61K 31/4704 | (2006.01) |
| C07D 215/26 | (2006.01) |
| C07D 401/06 | (2006.01) |
| A61K 31/4462 | (2006.01) |
| C07D 487/04 | (2006.01) |
| A61K 31/519 | (2006.01) |

(52) U.S. Cl. .................. 514/484; 560/115; 560/31; 560/32; 560/33; 560/29; 560/27; 560/28; 560/13; 560/22; 514/561; 514/485; 514/486; 514/480; 514/481; 514/487; 514/236.2; 514/249; 514/254.09; 514/253.08; 514/252.16; 514/263.4; 514/275; 514/247; 514/274; 514/316; 514/253.04; 514/300; 514/356; 514/351; 514/317; 514/327; 514/311; 514/312; 514/38; 514/34; 514/377; 514/365; 514/367; 514/415; 514/395; 514/359; 514/397; 514/400; 514/396; 514/398; 514/413; 536/13.7; 536/13.6; 536/6.4; 544/134; 544/260; 544/373; 544/363; 544/279

(58) Field of Classification Search ................ 558/240; 514/484, 563; 560/115, 27, 29
See application file for complete search history.

(56) References Cited

U.S. PATENT DOCUMENTS

| | | | |
|---|---|---|---|
| 3,845,770 A | 11/1974 | Theeuwes et al. | |
| 3,916,899 A | 11/1975 | Theeuwes et al. | |
| 4,024,175 A | 5/1977 | Satzinger et al. | |
| 4,087,544 A | 5/1978 | Satzinger et al. | |

| | | | |
|---|---|---|---|
| 4,426,391 | A | 1/1984 | Alexander et al. |
| 4,760,057 | A | 7/1988 | Alexander |
| 4,916,230 | A | 4/1990 | Alexander |
| 5,084,479 | A | 1/1992 | Woodruff |
| 5,112,598 | A | 5/1992 | Biesalski |
| 5,401,868 | A | 3/1995 | Lund |
| 5,556,611 | A | 9/1996 | Biesalski |
| 5,563,175 | A | 10/1996 | Silverman et al. |
| 5,698,155 | A | 12/1997 | Grosswald et al. |
| 5,733,907 | A | 3/1998 | Alexander et al. |
| 6,001,876 | A | 12/1999 | Singh |
| 6,020,370 | A | 2/2000 | Horwell et al. |
| 6,028,214 | A | 2/2000 | Silverman et al. |
| 6,103,932 | A | 8/2000 | Horwell et al. |
| 6,117,906 | A | 9/2000 | Silverman et al. |
| 2002/0107208 | A1 | 8/2002 | Chen et al. |
| 2003/0083382 | A1* | 5/2003 | Cundy et al. ............... 514/561 |
| 2003/0176398 | A1 | 9/2003 | Gallop et al. |
| 2004/0077553 | A1* | 4/2004 | Gallop et al. ............... 514/19 |

FOREIGN PATENT DOCUMENTS

| | | |
|---|---|---|
| EP | 0416689 | 3/1991 |
| EP | 1088819 | 4/2001 |
| JP | 2001002690 | 1/2001 |
| WO | WO 92/09560 | 6/1992 |
| WO | WO 93/23383 | 11/1993 |
| WO | WO 95/20567 | 8/1995 |
| WO | WO 96/40156 | 12/1996 |
| WO | WO 97/29101 | 8/1997 |
| WO | WO 97/33858 | 9/1997 |
| WO | WO 97/33859 | 9/1997 |
| WO | WO 98/17627 | 4/1998 |
| WO | WO 99/08671 | 2/1999 |
| WO | WO 99/21824 | 5/1999 |
| WO | WO 99/31057 | 6/1999 |
| WO | WO 99/31075 | 6/1999 |
| WO | WO 99/37296 | 7/1999 |
| WO | WO 99/61424 | 12/1999 |
| WO | WO 00/23067 | 4/2000 |
| WO | WO 00/31020 | 6/2000 |
| WO | WO 00/50027 | 8/2000 |
| WO | WO 00/59913 | 10/2000 |
| WO | WO 02/00209 | 1/2002 |
| WO | WO 02/28411 | 4/2002 |

OTHER PUBLICATIONS

CAS printout, downloaded Apr. 25, 2008, pp. 1-23.*
Alderman, "A Review of Cellulose Ethers in Hydrophilic Matrices for Oral Controlled-Release Dosage Forms," Int. J. Pharm. Tech. & Prod. Mfr. (1984) 5(3):1-9.
Bal-Tembe et al, "HL 752: A Potent and Long-Acting Antispasmodic Agent," Bioorg. Med. Chem. (1997) 5:1381-1387.
Bamba et al., "Release Mechanisms In Gelforming Sustained Release Preparations," Int. J. Pharm. (1979) 2:307-315.
Beller et al., "Transition Metals for Organic Synthesis," Chapter 2, Wiley VCH; Stewart, Current Organic Chemistry, (1998) 2:195-218.
Charpiot et al., "Disease Activated Drugs: A New Concept for the Treatment of Asthma," Bioorg. Med. Chem. (2001) 9:1793-1805.
During et al., "Controlled Release of Dopamine from a Polymeric Brain Implant; In Vivo Characterization," Ann. Neurol. (1989) 25:351-356.
Goodson, "Dental Applications" Medical Applications of Controlled Release (1984) 2: 115-138.
Guzzo, Peter R., "Preparation Of Optically Active (Acyloxy)Alkyl Esters From Optically Active O-acyl-.alpha.-Hydroxy Acids," Tetrahedron Letters, (2000) 5685-5689. 43.
Hong et al., "1-.beta.-D- Arabinofuranosylcytosine Conjugates of Corticosteroids as Potential Antitumor Agents," Eur. J. Cancer Clin. Oncol. (1983) 19:1105-1112.
Howard et al., "Intracerebral Drug Delivery in Rats with Lesion-induced Memory Deficits," J. Neurosurg. (1989) 71:105-112.
Kayser et al., "Designer Yeast: an Enantioselective Oxidizing Reagent for Organic Synthesis," Synlett(1999) 1:153-158.
Langer et al., "Chemical and Physical Structure of Polymers as Carriers for Controlled Release of Bioactive Agents: A Review," J Macromol. Sci. Rev. Macromol Chem. (1983) 23:61-126.
Langer, "New Methods of Drug Delivery," Science (1990) 249: 1527-1533.
Levy et al., "Inhibition of Calcification of Bioprosthetic Heart Valves by Local Controlled-Release Diphosphonate," Science (1985) 228:190-2.
Machrouhi et al., "Nucleophilic Acylation of Esters by Acid Chlorides Mediated by Samarium Diiodide: Formation and Use of Samarium Enediolates," Tetrahedron Lett. (1997), 38:7138-7186.
Martre et al., "Deprotection of Carbonyl Groups By Anodic Oxidation of Dithioacetals: A Key Step In the Synthesis of .alpha.-Diones,.alpha.-Ketols and Chiral Synthons," Tetrahedron Lett. (1990), 31: 2599-2602.
Renz et al., "100 Years of Baeyer-Villiger Oxidations," Eur. J. Org. Chem. (1999), 737-750.
Sakamoto et al., "Studies on Prodrugs. IV. Preparation and Characterization of N-(5-Substituted 2-oxo-1,3-dioxol-4-yl)methyl Norfloxacin," Chem. Pharm. Bull. (1985) 33:4870-4877.
Sasaki, Yoshiyuki, "Reaction of Carbon Dioxide with Propargyl Alcohol Catalyzed By A Combination of RU.sub.3 (CO).sub.13 and Et.sub.3 N," Tetrahedron Letters. 1986, vol. 27, No. 14, pp. 1573-1574.
Saudek et al., "A Preliminary Trial of the Programmable Implantable Medication System for Insulin Delivery," N. Engl. J Med. (1989) 321:574-579.
Stewart, "Cyclohexanone Monooxygenase: A Useful Reagent for Asymmetric Baeyer-Villiger Reactions," Current Organic Chemistry (1998), 2:195-216.
Strukul, "Transition Metal Catalysis in the Baeyer-Villiger Oxidation of Ketones," Angew. Chem. Int. Ed. (1998), 37:1198-1209.
Verma et al., "Osmotically Controlled Oral Drug Delivery," Drug Develop. Indus. Pharm. (2000), 26(7): 695-708.
Wermuth, C.G. et al, Glossary of Terms Used in Medicinal Chemistry, International Union of Pure and Applied Chemistry [retrieved on Nov. 17, 2004]. dated 1998 Retreived from the Internet <http://www.chem.qmw.ac.uk/iupac/medchem/ah.html>.

* cited by examiner

*Primary Examiner*—Brenda L Coleman
*Assistant Examiner*—Susanna Moore
(74) *Attorney, Agent, or Firm*—Dorsey & Whitney LLP

(57) ABSTRACT

The present invention provides a method for synthesizing 1-(acyloxy)-alkyl derivatives from 1-acyl-alkyl derivatives, which typically proceeds stereospecifically, in high yield, does not require the use of activated intermediates and/or toxic compounds and is readily amendable to scale-up. The current invention also provides 1-acyl-alkyl derivatives of known drug components and methods for synthesizing these 1-acyl-alkyl derivatives.

10 Claims, No Drawings

METHODS FOR SYNTHESIS OF PRODRUGS FROM 1-ACYL-ALKYL DERIVATIVES AND COMPOSITIONS THEREOF

This application is a continuation of prior U.S. patent application Ser. No. 10/167,797 filed Jun. 11, 2002, issued as U.S. Pat. No. 6,927,036, which claims benefit under 35 U.S.C. § 119(e) from U.S. Provisional Patent Application No. 60/358,603 filed Feb. 19, 2002; and U.S. Provisional Patent Application No. 60/371,535, filed Apr. 9, 2002, which are herein incorporated by reference.

1. FIELD OF THE INVENTION

The present invention relates generally to methods for synthesis of 1-(acyloxy)-alkyl derivatives. More particularly, the present invention relates to the synthesis of prodrugs (i.e., 1-(acyloxy)-alkyl derivatives of pharmacologically effective drugs) from 1-acyl-alkyl derivatives of pharmacologically effective drugs and to new compounds which are 1-acyl-alkyl derivatives of pharmacologically effective drugs.

2. BACKGROUND OF THE INVENTION

One solution to drug delivery and/or bioavailability issues in pharmaceutical development is converting known drugs to prodrugs. Typically, in a prodrug, a polar functional group (e.g., a carboxylic acid, an amino group, a hydroxyl group, etc.) is masked by a promoiety, which is labile under physiological conditions. Accordingly, prodrugs are usually transported through hydrophobic biological barriers such as membranes and typically possess superior physicochemical properties in comparison to the parent drug.

Pharmacologically effective prodrugs are non-toxic and are preferably selectively cleaved at the locus of drug action. Ideally, cleavage of the promoiety occurs rapidly and quantitatively with the formation of non-toxic by-products (i.e., the hydrolyzed promoiety).

The acyloxyalkoxycarbonyl functionality is an example of a promoiety that may be used to modulate the physiochemical properties of pharmaceuticals (Alexander, U.S. Pat. No. 4,916,230; Alexander, U.S. Pat. No. 5,733,907; Alexander et al., U.S. Pat. No. 4,426,391). Typically, 1-(acyloxy)-alkyl derivatives of pharmaceuticals possess superior bioavailability, are usually less irritating to topical and gastric mucosal membranes and more permeable through such membranes, when compared to the parent drugs.

However, although 1-(acyloxy)-alkyl ester derivatives of alcohols and 1-(acyloxy)-alkyl carbamate derivatives of amines have been frequently used to mask these polar functional groups in pharmaceuticals, existing synthetic methods for preparing these desirable prodrugs are inadequate. Existing methods for synthesis of acyloxyalkyl esters and carbamates are typically multi-step routes that utilize unstable intermediates and/or toxic compounds or salts and are difficult to perform on a process scale (Alexander, U.S. Pat. No. 4,760,057; Lund, U.S. Pat. No. 5,401,868; Alexander, U.S. Pat. No. 4,916,230; Saari et al., European Patent 0416689B1).

Although, 1-acyl-alkyl derivatives of drugs are known in the art (Sakamoto et al, Chem. Pharm. Bull. 1985, 33, 4870-4877; Hayashibe et al, International Publication No. WO 00/59913; Hartmann et al, International Publication No. WO 96/40156; Bal-Tembe et al, Bioorg. Med. Chem. 1997, 5, 1381-1387; Dow et al, European Patent Application No. EP1088819; Hong et al, Eur. J. Cancer Clin. Oncol. 1983, 19, 1105-1112; Ogata, K. Jpn. Kokai Tokkyo Koho JP 2001002690; Ashton et al, International Publication No. WO 95/20567; and Charpiot et al, Bioorg. Med. Chem. 2001, 9, 1793-1805) these compounds have not been converted to 1-(acyloxy)-alkyl prodrug derivatives. Accordingly, there is a need for a new synthesis of 1-(acyloxy)-alkyl derivatives that proceeds rapidly and efficiently, without the use of activated intermediates and/or toxic compounds, which is amenable to scale-up and proceeds through readily accessible synthetic precursors. Further, there is also a need for 1-acyl-alkyl derivatives, which may serve as synthetic precursors to 1-(acyloxy)-alkyl derivatives.

3. SUMMARY OF THE INVENTION

The present invention satisfies these and other needs by providing a method for synthesizing 1-(acyloxy)-alkyl derivatives from 1-acyl-alkyl derivatives, which typically proceeds stereospecifically, in high yield, does not require the use of activated intermediates and/or toxic compounds and which may provide process scale amounts of 1-(acyloxy)-alkyl compounds. The instant invention also provides 1-acyl-alkyl derivatives of known drug compounds and methods for synthesizing these 1-acyl-alkyl derivatives In one aspect, the present invention provides 1-acyl-alkyl derivatives comprising compounds of structural Formula (I):

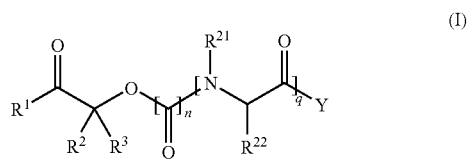

or a pharmaceutically acceptable salt, hydrate or solvate thereof, wherein:

n is 0 or 1;

q is 0 or 1;

provided that n and q are 0 unless Y is —NRR' or —OR;

Y is —NRR', —OR, —C(O)R, —P(O)(OR')R or —P(O)(OR')(OR), wherein:

—NRR' is derived from a drug containing a primary or secondary amino group, with the proviso that the drug is not norfloxacin, pamidronate or a 2-aminomethyl-3-methylthiazolo[3,2a]benzimidazole derivative;

—OR is derived from a drug containing a hydroxyl group, with the proviso that the drug is not 1-hydroxymethyl 5-fluorouracil or a 1-aryl-6,7-dialkoxyisoquinolone phosphodiesterase inhibitor;

—OC(O)R is derived from a drug containing a carboxylic acid or carboxylate group, with the proviso that the drug is not a 6-azauracil-5-carboxylic acid derivative;

—OP(O)(OR')R is derived from a drug containing a phosphonic acid or phosphonate group;

—OP(O)(OR')(OR) is derived from a drug containing a phosphoric acid or phosphate group, with the proviso that the drug is not cytarabine-5'-phosphate or α-tocopherol phosphate;

$R^1$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl or a $C_{23}$ bile acid moiety or optionally, $R^1$ and either $R^2$ or $R^3$, together with the atoms to which $R^1$ and $R^2$ or $R^3$ are attached, form a cycloalkyl, substituted cycloalkyl, cycloheteroalkyl or substituted cycloheteroalkyl ring, which is optionally fused to an aryl, substituted aryl, heteroaryl, substituted heteroaryl, cycloalkyl, substituted cycloalkyl, cycloheteroalkyl or substituted cycloheteroalkyl ring;

$R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl or substituted heteroarylalkyl or optionally, $R^2$ and $R^3$ together with the atom to which they are attached form a cycloalkyl, substituted cycloalkyl, cycloheteroalkyl or substituted cycloheteroalkyl ring;

$R^{21}$ is independently hydrogen, alkyl or substituted alkyl; and $R^{22}$ is independently hydrogen, alkyl, substituted alkyl, alkoxy, substituted alkoxy, acyl, substituted acyl, acylamino, substituted acylamino, alkylamino, substituted alkylamino, alklysulfinyl, substituted alkylsulfinyl, alkylsulfonyl, substituted alkylsulfonyl, alkylthio, substituted alkylthio, alkoxycarbonyl, substituted alkylthio, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy, substituted heteroaryloxy or optionally, $R^{22}$ together with the carbon atom to which it is attached, the adjacent nitrogen atom and $R^{21}$ substituent form a cycloheteroalkyl or substituted cycloheteroalkyl ring.

In another aspect, the present invention provides a method of synthesizing a 1-(acyloxy)-alkyl derivative of structural Formula (II), which comprises oxidation of a compound of structural Formula (I) by contacting the compound of Formula (I) with an oxidant to form a compound of Formula (II):

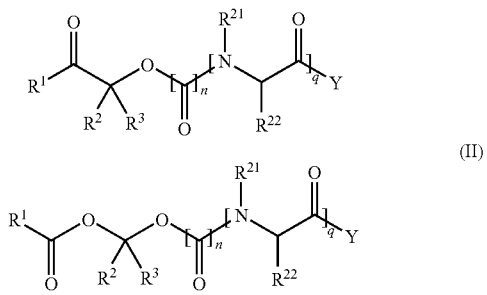

(II)

where n, q, Y, $R^1$, $R^2$, $R^3$, $R^{21}$, $R^{22}$ and q are as defined above. The oxidant may be an organism (e.g., yeast or bacteria) or a chemical reagent (e.g., an enzyme or a peroxide).

4. DETAILED DESCRIPTION OF THE INVENTION

4.1 Definitions

"Compounds of the invention" refers to compounds encompassed by structural Formulae (I), (IV) and (V) disclosed herein, and includes any specific compounds within these Formulae whose structure is disclosed herein. The compounds of the invention may be identified either by their chemical structure and/or chemical name. When the chemical structure and chemical name conflict, the chemical structure is determinative of the identity of the compound. The compounds of the invention may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically. pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention also include isotopically labeled compounds where one or more atoms have an atomic mass different from the atomic mass conventionally found in nature. Examples of isotopes that may be incorporated into the compounds of the invention include, but are not limited to $^2$H, $^3$H, $^{13}$C, $^{14}$C, $^{15}$N, $^{18}$O, $^{17}$O, $^{31}$P, $^{32}$P, $^{35}$S, $^8$F and $^{36}$Cl. Further, it should be understood, when partial structures of the compounds of the invention are illustrated, that brackets of dashes indicate the point of attachment of the partial structure to the rest of the molecule.

"Composition of the invention" refers to at least one compound of the invention and a pharmaceutically acceptable vehicle, with which the compound is administered to a patient. When administered to a patient, the compounds of the invention are administered in isolated form, which means separated from a synthetic organic reaction mixture.

"1-Acyl-Alkyl Derivatives" refers to N-1-acyl-alkoxycarbonyl derivatives of a primary or secondary amine; O-1-acyl-alkoxycarbonyl derivatives of an alcohol; 1-acyl-alkyl esters of a carboxylic acid; 1-acyl-alkyl esters of a phosphonic acid; and 1-acyl-alkyl esters of a phosphoric acid.

"1-(Acyloxy)-Alkyl Derivatives" refers to N-1-(acyloxy)-alkoxycarbonyl derivatives of a primary or secondary amine; O-1-(acyloxy)-alkoxycarbonyl derivatives of an alcohol; 1-(acyloxy)-alkyl esters of a carboxylic acid; 1-(acyloxy)-alkyl esters of a phosphonic acid; and 1-(acyloxy)-alkyl esters of a phosphoric acid.

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 20 carbon atoms, more preferably, from 1 to 10 carbon atoms.

"Alkanyl" refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to formyl, acetyl, cyclohexylcarbonyl, cyclohexylmethylcarbonyl, benzoyl, benzylcarbonyl and the like.

"Acylamino" refers to a radical —NR'C(O)R, where R' and R are each independently hydrogen, alkyl, cycloalkyl, cycloheteroalkyl, aryl, arylalkyl, heteroalkyl, heteroaryl, heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Alkylamino" means a radical —NHR where R represents an alkyl or cycloalkyl group as defined herein. Representative examples include, but are not limited to, methylamino, ethylamino, 1-methylethylamino, cyclohexyl amino and the like.

"Alkoxy" refers to a radical —OR where R represents an alkyl or cycloalkyl group as defined herein. Representative examples include, but are not limited to, methoxy, ethoxy, propoxy, butoxy, cyclohexyloxy and the like.

"Alkoxycarbonyl" refers to a radical —C(O)-alkoxy where alkoxy is as defined herein.

"Alkylsulfonyl" refers to a radical —S(O)$_2$R where R is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR where R is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Aryl" refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms, more preferably, between 6 to 12 carbon atoms.

"Arylalkyl" refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is (C$_6$-C$_{30}$) arylalkyl, e.g., the alkanyl, alkenyl or alkynyl moiety of the arylalkyl group is (C$_1$-C$_{10}$) and the aryl moiety is (C$_6$-C$_{20}$), more preferably, an arylalkyl group is (C$_6$-C$_{20}$) arylalkyl, e.g., the alkanyl, alkenyl or alkynyl moiety of the arylalkyl group is (C$_1$-C$_8$) and the aryl moiety is (C$_6$-C$_{12}$).

"Arylalkyloxy" refers to an —O-arylalkyl radical where arylalkyl is as defined herein.

"Aryloxycarbonyl" refers to a radical —C(O)—O-aryl where aryl is as defined herein.

"C$_{23}$ bile acid moiety" refers to a fragment derived from naturally occurring bile acids by removal of the carboxyl group. Preferred C$_{23}$ bile acid moieties are derived from the following structures:

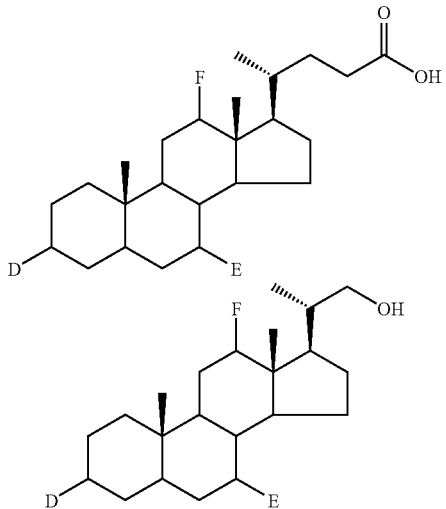

where $R^4$ and $R^5$ are both α-OH or $R^4$ is β-OH and $R^5$ is hydrogen or $R^4$ is α-OH and $R^5$ is hydrogen or $R^4$ is hydrogen and $R^5$ is α-OH or $R^4$ is β-OH and $R^5$ is α-OH or $R^4$ and $R^5$ are both hydrogen.

"Carbamoyl" refers to the radical —C(O)N(R)$_2$ where each R group is independently hydrogen, alkyl, cycloalkyl or aryl as defined herein, which may be optionally substituted as defined herein.

"Carboxy" means the radical —C(O)OH.

"Cyano" means the radical —CN.

"Cycloalkyl" refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In a preferred embodiment, the cycloalkyl group is ($C_3$-$C_{10}$) cycloalkyl, more preferably ($C_3$-$C_7$) cycloalkyl.

"Cycloheteroalkyl" refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Cycloheteroalkyloxycarbonyl" refers to a radical —C(O)—OR where R is cycloheteroalkyl as defined herein.

"Dialkylamino" means a radical —NRR' where R and R' independently represent an alkyl or cycloalkyl group as defined herein. Representative examples include, but are not limited to dimethylamino, methylethylamino, di-(1-methylethyl)amino, (cyclohexyl)(methyl)amino, (cyclohexyl)(ethyl)amino, (cyclohexyl)(propyl)amino, and the like.

"Derived from a drug" refers to a fragment that is structurally related to such a drug. The structure of the fragment is identical to the drug except where a hydrogen atom attached to a heteroatom (N or O) has been replaced with a covalent bond to another group (typically, a promoiety). Note that when a drug is a salt form of a carboxylic, phosphonic or phosphoric acid, the corresponding structural fragment derived from such a drug is considered to derived from the protonated acid form.

"Drug" refers to a compound that exhibits therapeutic and/or prophylactic and/or diagnostic utility when administered in effective amounts to a mammal.

"Halo" means fluoro, chloro, bromo, or iodo.

"Heteroalkyloxy" means an —O-heteroalkyl radical where heteroalkyl is as defined herein.

"Heteroalkyl, Heteroalkanyl, Heteroalkenyl, Heteroalkynyl" refer to alkyl, alkanyl, alkenyl and alkynyl groups, respectively, in which one or more of the carbon atoms (and any associated hydrogen atoms) are each independently replaced with the same or different heteroatomic groups. Typical heteroatomic groups include, but are not limited to, —O—, —S—, —O—O—, —S—S—, —O—S—, —NR'—, =N—N=, —N=N—, —N=N—NR'—, —PH—, —P(O)$_2$—, —O—P(O)$_2$—, —S(O)—, S(O)$_2$—, —SnH$_2$— and the like, wherein R' is hydrogen, alkyl, substituted alkyl, cycloalkyl, substituted cycloalkyl, aryl or substituted aryl.

"Heteroaryl" refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, Ǝ-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-20 membered heteroaryl, with 5-10 membered heteroaryl being particularly preferred. Preferred heteroaryl groups are those derived from thiophene, pyrrole, benzothiophene, benzofuran, indole, pyridine, quinoline, imidazole, oxazole and pyrazine.

"Heteroaryloxycarbonyl" refers to a radical —C(O)—OR where R is heteroaryl as defined herein.

"Heteroarylalkyl" refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. Preferably, the heteroarylalkyl radical is a 6-30 membered heteroarylalkyl, e.g., the alkanyl, alkenyl or alkynyl moiety of the heteroarylalkyl is 1-10 membered and the heteroaryl moiety is a 5-20 membered heteroaryl, more preferably, a 6-20 membered heteroarylalkyl, e.g., the alkanyl, alkenyl or alkynyl moiety of the heteroarylalkyl is 1-8 membered and the heteroaryl moiety is a 5-12 membered heteroaryl.

"Hydroxy" means the radical —OH.

"Oxo" means the divalent radical =O.

"Pharmaceutically acceptable" means approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention, which is pharmaceutically acceptable and possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Patient" includes humans. The terms "human" and "patient" are used interchangeably herein.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Prodrugs are frequently (though not necessarily) pharmacologically inactive until converted to the parent drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting goup" refers to a grouping of atoms that when attached to a reactive group in a molecule masks, reduces or prevents that reactivity. Examples of protecting groups can be found in Green et aL, "Protective Groups in Organic Chemistry", (Wiley, $_2$nd ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Racemate" refers to an equimolar mixture of enantiomers of a chiral molecule.

"Substituted" refers to a group in which one or more hydrogen atoms are each independently replaced with the same or different substituent(s). Typical substituents include, but are not limited to, —X, —$R^{14}$, —$O^-$, =O, —$OR^{14}$, —$SR^{14}$, —$S^-$, =S, —$NR^{14}R^{15}$, =$NR^{14}$, —$CX_3$, —$CF_3$, —CN, —OCN, —SCN, —NO, —$NO_2$, =$N_2$, —$N_3$, —$S(O)_2O^-$, —$S(O)_2OH$, —$S(O)_2R^{14}$, —$OS(O_2)O^-$, —$OS(O)_2R^{14}$, —$P(O)(O^-)_2$, —$P(O)(OR^{14})(O^-)$, —$OP(O)(OR^{14})(OR^{15})$, —$C(O)R^{14}$, —$C(S)R^{14}$, —$C(O)OR^{14}$, —$C(O)NR^{14}R^{15}$, —$C(O)O^-$, —$C(S)OR^{14}$, —$NR^{16}C(O)NR^{14}R^{15}$, $NR^{16}C(S)$ $NR^{14}R^{15}$, —$NR^{17}C(NR^{16})NR^{14}$ $R^{15}$ and —$C(NR^{16})$ $NR^{14}R^{15}$, where each X is independently a halogen; each $R^{14}$, $R^{15}$, $R^{16}$ and $R^{17}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —$NR^{18}R^{19}$, —$C(O)R^{18}$ or —$S(O)_2R^{18}$ or optionally $R^{18}$ and $R^{19}$ together with the atom to which they are both attached form a cycloheteroalkyl or substituted cycloheteroalkyl ring; and $R^{18}$ and $R^{19}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Thio" means the radical —SH.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

4.2 Compounds of the Invention

The present invention provides 1-acyl-alkyl derivatives of structural Formula (I):

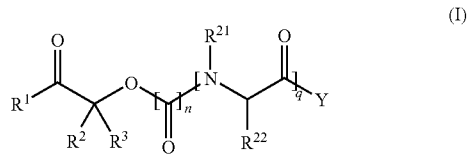

(I)

or a pharmaceutically acceptable salt, hydrate or solvate thereof, wherein:

n, q, Y, $R^1$, $R^2$, $R^3$, $R^{21}$ and $R^{22}$ are as defined above.

Compounds of Formula (I) may be synthetic intermediates in the preparation of 1-(acyloxy)-alkyl derivatives. Alternatively, compounds of Formula (I) may be protected versions of drug molecules, where the 1-acyl-alkyl.portion of the molecule masks a reactive functionality such as amino group, hydroxyl, etc. Accordingly, compounds of Formula (I) may be prodrugs of drug molecules and/or may be useful in the synthesis of novel drug derivatives.

In one embodiment, q is 0. In this embodiment, the present invention provides 1-acyl-alkyl derivatives of structural Formula (III):

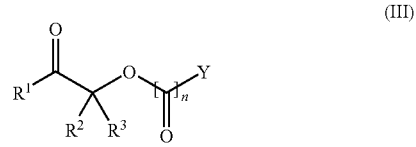

(III)

where n, Y, $R^1$, $R^2$ and $R^3$ are as previously defined. In another embodiment, q is 1.

In one embodiment of compounds of structural Formula (I), $R^{21}$ is hydrogen or alkyl. Preferably, $R^{21}$ is hydrogen, methyl, ethyl, propyl or butyl, more preferably, $R^{21}$ is hydrogen or methyl.

In another embodiment of compounds of Formula (I), $R^{22}$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl or optionally, together with the carbon atom to which it is attached and the adjacent nitrogen atom forms a cycloheteroalkyl or substituted cycloheteroalkyl ring. Preferably, $R^{22}$ is hydrogen, alkanyl, substituted alkanyl, aryl, substituted aryl, arylalkanyl, substituted arylalkanyl, cycloalkanyl, heteroarylalkanyl and substituted heteroarylalkanyl or optionally, $R^{22}$ together with the carbon atom to which it is attached, the adjacent nitrogen atom and $R^{21}$ substituent form a cycloheteroalkyl or substituted cycloheteroalkyl ring.

In still another embodiment, $R^{22}$ together with the carbon atom to which it is attached, the adjacent nitrogen atom and $R^{21}$ form a five membered ring. In still another embodiment, $R^{22}$ is hydrogen, cycloalkanyl or alkanyl. Preferably, $R^{22}$ is hydrogen, methyl, 2-propyl, 2-butyl, isobutyl, t-butyl, cyclopentyl or cyclohexyl.

In still another embodiment, $R^{22}$ is substituted alkanyl. Preferably, $R^{22}$ is —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, $CH_2SH$, —$CH_2(CH_2)_3NH_2$ or —$CH_2CH_2CH_2NHC(NH)NH_2$.

In still another embodiment, $R^{22}$ is selected from the group consisting of aryl, arylalkanyl, substituted arylalkanyl and heteroarylalkanyl. Preferably, $R^{22}$ is phenyl, benzyl, 4-hydroxybenzyl, 2-imidazolyl or 2-indolyl.

In one embodiment, $R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl. Preferably, $R^2$ and $R^3$ are independently hydrogen, alkyl, alkoxycarbonyl, aryl, arylalkyl, carbamoyl, cycloalkoxycarbonyl or heteroaryl. In one embodiment, when $R^2$ is alkoxycarbonyl, cycloalkoxycarbonyl or carbamoyl then $R^3$ is methyl. More preferably, R and $R^3$ are independently hydrogen, methyl, ethyl, propyl, isopropyl, butyl, isobutyl, sec-butyl, tert-butyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclohexyloxycarbonyl, phenyl, benzyl, phenethyl or 3-pyridyl.

In still another embodiment, $R^2$ and $R^3$ are independently hydrogen, alkanyl or substituted alkanyl. More preferably, $R^2$ and $R^3$ are hydrogen or alkanyl. Even more preferably, $R^2$ and $R^3$ are independently hydrogen, methyl, ethyl, propyl, isopropyl or butyl.

In still another embodiment, $R^2$ and $R^3$ are independently hydrogen, aryl, arylalkyl or heteroaryl. More preferably, $R^2$ and $R^3$ are independently hydrogen, phenyl, benzyl, phenethyl or 3-pyridyl. Most preferably, $R^2$ is hydrogen and $R^3$ is hydrogen; $R^2$ is methyl and $R^3$ is hydrogen; $R^2$ is ethyl and $R^3$ is hydrogen; $R^2$ is propyl and $R^3$ is hydrogen; $R^2$ is isopropyl and $R^3$ is hydrogen; $R^2$ is butyl and $R^3$ is hydrogen; $R^2$ is phenyl and $R^3$ is hydrogen; $R^2$ is methoxycarbonyl and $R^3$ is methyl; $R^2$ is ethoxycarbonyl and $R^3$ is methyl; $R^2$ is isopropoxycarbonyl and $R^3$ is methyl; and $R^2$ is methyl and $R^3$ is methyl.

In still another embodiment, $R^1$ is hydrogen, alkyl, substituted alkyl, aryl, substituted aryl, arylalkyl, substituted arylalkyl, cycloalkyl, substituted cycloalkyl, heteroaryl, substituted heteroaryl or a $C_{23}$ bile acid moiety. Preferably, $R^1$ is hydrogen, alkyl, substituted alkyl, aryl, arylalkyl, cycloalkyl or heteroaryl. More preferably, $R^1$ is methyl, ethyl, propyl, isopropyl, butyl, isobutyl, sec-butyl, tert-butyl, pentyl, isopentyl, sec-pentyl, neopentyl, cyclobutyl, cyclopentyl, cyclohexyl, phenyl, 4-methoxyphenyl, benzyl, phenethyl, styryl or 3-pyridyl.

In still another embodiment, $R^1$ is alkanyl or substituted alkanyl or a $C_{23}$ bile acid moiety. More preferably, $R^1$ is methyl, ethyl, propyl, isopropyl, butyl, isobutyl, sec-butyl, tert-butyl, pentyl, isopentyl, sec-pentyl or neopentyl. Most preferably, $R^1$ is hydrogen, methyl, ethyl, propyl, isopropyl or butyl.

In still another embodiment, $R^1$ is hydrogen, aryl, arylalkyl or heteroaryl. More preferably, $R^1$ is phenyl, 4-methoxyphenyl, benzyl, phenethyl, styryl or 3-pyridyl.

In still another embodiment, $R^1$ and either $R^2$ or $R^3$, together with the atoms to which $R^1$ and $R^2$ or $R^3$ are attached, form a cycloalkyl or substituted cycloalkyl ring, which is optionally fused to an aryl, substituted aryl, heteroaryl or substituted heteroaryl ring. Preferably, $R^1$ and either $R^2$ or $R^3$, together with the atoms to which $R^1$ and $R^2$ or $R^3$ are attached, form a cyclobutyl, cyclopentyl or cyclohexyl ring.

In still another embodiment, $R^2$ and $R^3$ together with the atom to which they are attached form a cycloalkyl or substituted cycloalkyl ring. Preferably, $R^2$ and $R^3$ together with the atom to which they are attached form a cyclobutyl, cyclopentyl or cyclohexyl ring.

In still another embodiment, $R^1$ is hydrogen, alkyl, substituted alkyl, aryl, substituted aryl, arylalkyl, substituted arylalkyl, cycloalkyl, substituted cycloalkyl, heteroaryl or substituted heteroaryl and $R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl. Preferably, when $R^2$ is alkoxycarbonyl, cycloalkoxycarbonyl or carbamoyl then $R^3$ is methyl. More preferably, $R^1$ is methyl, ethyl, propyl, isopropyl, butyl, isobutyl, sec-butyl, tert-butyl, pentyl, isopentyl, sec-pentyl, neopentyl, cyclobutyl, cyclopentyl, cyclohexyl, phenyl, 4-methoxyphenyl, benzyl, phenethyl, styryl or 3-pyridyl and $R^2$ and $R^3$ are hydrogen, methyl, ethyl, propyl, isopropyl, butyl, isobutyl, sec-butyl, tert-butyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclohexyloxycarbonyl, phenyl, benzyl, phenethyl or 3-pyridyl.

In still another embodiment, $R^1$ is hydrogen, alkyl, substituted alkyl, aryl, substituted aryl, arylalkyl, substituted arylalkyl, cycloalkyl, substituted cycloalkyl, heteroaryl or substituted heteroaryl and $R^2$ and $R^3$ together with the atom to which they are attached form a cycloalkyl, substituted cycloalkyl, cycloheteroalkyl or substituted cycloheteroalkyl ring. Preferably, $R^1$ is hydrogen, alkyl, substituted alkyl, aryl, arylalkyl or heteroaryl and $R^2$ and $R^3$ together with the atom to which they are attached form a cycloalkyl or substituted cycloalkyl ring. More preferably, $R^1$ is methyl, ethyl, propyl, isopropyl, butyl, isobutyl, sec-butyl, tert-butyl, pentyl, isopentyl, sec-pentyl, neopentyl, cyclobutyl, cyclopentyl, cyclohexyl, phenyl, 4-methoxyphenyl, benzyl, phenethyl, styryl or 3-pyridyl and $R^2$ and $R^3$ are independently form a cyclobutyl, cyclopentyl or a cyclohexyl ring.

In still another embodiment, $R^1$ is alkanyl or substituted alkanyl and $R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl. Preferably, $R^2$ is alkoxycarbonyl, cycloalkoxycarbonyl or carbamoyl and $R^3$ is methyl. More preferably, $R^1$ is methyl, ethyl, propyl, isopropyl or butyl, and $R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl. Preferably, $R^2$ is alkoxycarbonyl, cycloalkoxycarbonyl or carbamoyl and $R^3$ is methyl.

In still another embodiment, $R^1$ is a $C_{23}$ bile acid moiety and $R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl. Preferably, $R^2$ is alkoxycarbonyl, cycloalkoxycarbonyl or carbamoyl and $R^3$ is methyl.

In still another embodiment, $R^1$ is hydrogen, alkyl, substituted alkyl, aryl, substituted aryl, arylalkyl, substituted arylalkyl, cycloalkyl, substituted cycloalkyl, heteroaryl or substituted heteroaryl and $R^2$ and $R^3$ are independently hydrogen, alkyl, aryl, arylalkyl or heteroaryl. Preferably, $R^1$ is hydrogen, alkyl, substituted alkyl, aryl, arylalkyl or heteroaryl and $R^2$ and $R^3$ are independently hydrogen, alkanyl or substituted alkanyl. Even more preferably, $R^1$ is hydrogen, alkyl, substituted alkyl, aryl, arylalkyl or heteroaryl and $R^2$ and $R^3$ are independently hydrogen, methyl, ethyl, propyl, isopropyl, butyl, isobutyl, sec-butyl, tert-butyl or phenyl. Preferably, $R^1$ is hydrogen, alkyl, substituted alkyl, aryl, arylalkyl or heteroaryl and $R^2$ and $R^3$ together with the atom to which they are attached form a cycloalkyl, substituted cycloalkyl, cycloheteroalkyl or substituted cycloheteroalkyl ring. In the above embodiments, $R^1$ is preferably methyl, ethyl, propyl, isopropyl, butyl, isobutyl, sec-butyl, tert-butyl, pentyl, isopentyl, sec-pentyl, neopentyl, phenyl, 4-methoxyphenyl, benzyl, phenethyl, styryl or 3-pyridyl.

In still another embodiment, $R^1$ is hydrogen, alkyl, substituted alkyl, aryl, arylalkyl or heteroaryl and $R^2$ and $R^3$ are independently hydrogen, alkyl, aryl, arylalkyl or heteroaryl. More preferably, $R^1$ is hydrogen, alkyl, substituted alkyl, aryl, arylalkyl or heteroaryl and $R^2$ and $R^3$ are independently hydrogen, alkanyl or substituted alkanyl. Even more preferably, $R^1$ is hydrogen, alkyl, substituted alkyl, aryl, arylalkyl or heteroaryl or substituted cycloalkyl and $R^2$ and $R^3$ are independently hydrogen, methyl, ethyl, propyl, isopropyl, butyl, isobutyl, sec-butyl, tert-butyl or phenyl. Preferably, $R^1$ is hydrogen, alkyl, substituted alkyl, aryl, arylalkyl or heteroaryl and $R^2$ and $R^3$ together with the atom to which they are attached form a cycloalkyl, substituted cycloalkyl, cycloheteroalkyl or substituted cycloheteroalkyl ring. In the above embodiments, $R^1$ is preferably methyl, ethyl, propyl, isopropyl, butyl, isobutyl, sec-butyl, tert-butyl, pentyl, isopentyl, sec-pentyl, neopentyl, phenyl, 4-methoxyphenyl, benzyl, phenethyl, styryl or 3-pyridyl.

In still another embodiment, $R^1$ is alkanyl or substituted alkanyl and $R^2$ and $R^3$ are independently hydrogen, alkyl, aryl, arylalkyl or cycloalkyl. More preferably, $R^1$ is alkanyl or substituted alkanyl and $R^2$ and $R^3$ are independently hydrogen, alkanyl or substituted alkanyl. Even more preferably, $R^1$ is alkanyl or substituted alkanyl and $R^2$ and $R^3$ are independently hydrogen, methyl, ethyl, propyl, isopropyl, butyl, isobutyl, sec-butyl, tert-butyl or phenyl. Preferably, $R^1$ is alkanyl or substituted alkanyl and $R^2$ and $R^3$ together with the atom to which they are attached form a cycloalkyl, substituted cycloalkyl, cycloheteroalkyl or substituted cycloheteroalkyl ring. In the above embodiments, $R^1$ is preferably methyl, ethyl, propyl, isopropyl, butyl, isobutyl, sec-butyl or tert-butyl.

In still another embodiment, $R^1$ is a $C_{23}$ bile acid moiety and $R^2$ and $R^3$ are independently hydrogen, alkyl, aryl, arylalkyl or heteroaryl. Preferably, $R^1$ is a $C_{23}$ bile acid moiety and $R^2$ and $R^3$ are independently hydrogen, alkanyl or substituted alkanyl. More preferably, $R^1$ is a $C_{23}$ bile acid moiety and $R^2$ and $R^3$ are independently hydrogen, methyl, ethyl, propyl, isopropyl, butyl, isobutyl, sec-butyl, tert-butyl or phenyl. Preferably, $R^1$ is a $C_{23}$ bile acid moiety and $R^2$ or $R^3$ together with the atom to which they are attached form a cycloalkyl, substituted cycloalkyl, cycloheteroalkyl or substituted cycloheteroalkyl ring. Preferably, in the above embodiments, the $C_{23}$ bile acid moiety is cholic acid or ursodeoxycholic acid.

Examples of drugs which contain carboxyl groups (i.e., Y is —C(O)R) include, but are not limited to, angiotensin-converting enzyme inhibitors such as alecapril, captopril, 1-[4-carboxy-2-methyl-2R,4R-pentanoyl]-2,3-dihydro-2S-indole-2-carboxylic acid, enalaprilic acid, lisinopril, N-cyclopentyl-N-[3-[(2,2-dimethyl-1-oxopropyl)thio]-2-methyl-1-oxopropyl]glycine, pivopril, quinaprilat, (2R, 4R)-2-hydroxyphenyl)-3-(3-mercaptopropionyl)-4-thiazolidinecarboxylic acid, (S) benzamido-4-oxo-6-phenylhexenoyl-2-carboxypyrrolidine, [2S-1[R*(R*))]]2α,3αβ,7αβ]-1[2-[[1-carboxy-3-phenylpropyl]-amino]-1-oxopropyl]octahydro-1H-indole-2-carboxylic acid, [3S-1[R*(R*))]],3R*]-2-[2-[[1-carboxy-3-phenylpropyl]-amino]-1-oxopropyl]-1,2,3,4-tetrahydro-3-isoquinolone carboxylic acid and tiopronin; cephalosporin antibiotics such as cefaclor, cefadroxil, cefamandole, cefatrizine, cefazedone, cefazuflur, cefazolin, cefbuperazone, cefixime, cefinenoxime, cefmetazole, cefodizime, cefonicid, cefoperazone, cefuranide, cefotaxime, cefotefan, cefotiam, cefoxitin, cefpimizole, cefpirome, cefpodoxime, cefroxadine, cefsulodin, cefpiramide, ceftazidime, ceftezole, ceftizoxime, ceftriaxone, cefuroxime, cephacetrile, cephalexin, cephaloglycin, cephaloridine, cephalosporin, cephanone, cephradine and latamoxef; penicillins such as amoxycillin, ampicillin, apalcillin, azidocillin, azlocillin, benzylpencillin, carbenicillin, carfecillin, carindacillin, cloxacillin, cyclacillin, dicloxacillin, epicillin, flucloxacillin, hetacillin, methicillin, mezlocillin, nafcillin, oxacillin, phenethicillin, piperazillin, sulbenicllin, temocillin and ticarcillin; thrombin inhibitors such as argatroban, melagatran and napsagatran; influenza neuraminidase inhibitors such as zanamivir and BCX-1812; non-steroidal antiinflammatory agents such as acametacin, alclofenac, alminoprofen, aspirin (acetylsalicylic acid), 4-biphenylacetic acid, bucloxic acid, carprofen, cinchofen, cinmetacin, clometacin, clonixin, diclenofac, diflunisal, etodolac, fenbufen, fenclofenac, fenclosic acid, fenoprofen, ferobufen, flufenamic acid, flufenisal, flurbiprofin, fluprofen, flutiazin, ibufenac, ibuprofen, indomethacin, indoprofen, ketoprofen, ketorolac, lonazolac, loxoprofen, meclofenamic acid, mefenamic acid, 2-(8-methyl-10,11-dihydro-1-oxodibenz[b,f]oxepin-2-yl) propionic acid, naproxen, nifluminic acid, O-(carbamoylphenoxy)acetic acid, oxoprozin, pirprofen, prodolic acid, salicylic acid, salicylsalicylic acid, sulindac, suprofen, tiaprofenic acid, tolfenamic acid, tolmetin and zopemirac; prostaglandins such as ciprostene, 16-deoxy-16-hydroxy-16-vinyl prostaglandin $E_2$, 6,16-dimethylprostaglandin $E_2$, epoprostostenol, meteneprost, nileprost, prostacyclin, prostaglandins E1, $E_2$, or $F_{2\alpha}$ and thromboxane $A_2$; and quinolone antibiotics such as acrosoxacin, cinoxacin, ciprofloxacin, enoxacin, flumequine, naladixic acid, norfloxacin, ofloxacin, oxolinic acid, pefloxacin, pipemidic acid and piromidic acid; other antibiotics such as aztreonam, imipenem, meropenem and related carbopenem antibiotics.

In a preferred embodiment, drugs which contain carboxyl groups (i.e., Y is —C(O)R) include acametacin, argatroban, BCX-140, BCX-1812, cefotaxime, ceftazidime, ceftriaxone, cromolyn, foscamet, lamifiban, melagatran, meropenem and zanamivir.

Examples of drugs which contain amine groups (i.e., Y is —NRR'; and the amino fragment may be either primary (i.e., R' is hydrogen) or secondary) include, but are not limited to, acebutalol, albuterol, alprenolol, atenolol, bunolol, bupropion, butopamine, butoxamine, carbuterol, cartelolol, colterol, deterenol, dexpropanolol, diacetolol, dobutamine, exaprolol, exprenolol, fenyripol, labotolol, levobunolol, metolol, metaproterenol, metoprolol, nadolol, pamatolol, penbutalol, pindolol, pirbuterol, practolol, prenalterol, primidolol, prizidilol, procaterol, propanolol, quinterenol, rimiterol, ritodrine, solotol, soterenol, sulfiniolol, sulfinterol, sulictidil, tazaolol, terbutaline, timolol, tiprenolol, tipridil, tolamolol, thiabendazole, albendazole, albutoin, alendronate, alinidine, alizapride, amiloride, aminorex, aprinocid, cambendazole, cimetidine, clonidine, cyclobenzadole, delavirdine, efegatrin, etintidine, fenbendazole, fenmetazole, flubendazole, fludorex, gabapentin, icadronate, lobendazole, mebendazole, metazoline, metoclopramide, methylphenidate, mexiletine, neridronate, nocodazole, oxfendazole, oxibendazole, oxmetidine, pamidronate, parbendazole, pramipexole, prazosin, pregabalin, procainamide, ranitidine, tetrahydrazoline, tiamenidine, tinazoline, tiotidine, tocainide, tolazoline, tramazoline, xylometazoline, dimethoxyphenethylamine, N-[3(R)-[2-piperidin-4-yl)ethyl]-2-piperidone-1-yl]acetyl-3(R)-methyl-β-alanine, adrenolone, aletamine, amidephrine, amphetamine, aspartame, bamethan, betahistine, clorprenaline, chlortermine, dopamine, L-Dopa, ephrinephrine etryptamine, fenfluramine, methyldopamine, norepinephrine, tocainide, enviroxime, nifedipine, nimodipine, triamterene, pipedemic acid and similar compounds, 1-ethyl-6-fluoro-1,4dihydro-4-oxo-7-(1-piperazinyl)-1,8-napthyridine-3-carboxylic acid, 1-cyclopropyl-6-fluoro-1,4-dihydro-4-oxo-7-(piperazinyl)-3-quinolinecarboxylic acid.

In a preferred embodiment, drugs which contain primary or secondary amino groups (i.e., Y is —NR'R) include amifostine, baclofen, clonidine, ciprofloxacin, cisapride, daunorubicin, doxorubicin, fenoterol, gentamycin, kanamycin, levodopa, meropenem, metazoline, neomycin, tobramycin, trovafloxacin and vigabatrin.

Examples of drugs which contain hydroxy groups (i.e., Y is —OR) include, but are not limited to, steroidal hormones such as allylestrenol, cingestol, dehydroepiandrosteron, dienostrol, diethylstilbestrol, dimethisteron, ethyneron, ethynodiol, estradiol, estron, ethinyl estradiol, ethisteron, lynestrenol, mestranol, methyl testosterone, norethindron, norgestrel, norvinsteron, oxogeston, quinestrol, testosteron and tigestol; tranquilizers such as dofexazepam, hydroxyzin, lorazepam and oxazepam; neuroleptics such as acetophenazine, carphenazine, fluphenazine, perphenyzine and piperaetazine; cytostatics such as aclarubicin, cytarabine, decitabine, daunorubicin, dihydro-5-azacytidine, doxorubicin, epirubicin, estramustin, etoposide, fludarabine, gemcitabine, 7-hydroxychlorpromazin, nelarabine, neplanocin A, pentostatin, podophyllotoxin, tezacitabine, troxacitabine, vinblastin, vincristin, vindesin; hormones and hormone antagonists such as buserilin, gonadoliberin, icatibrant and leuprorelin acetate; antihistamines such as terphenadine; analgesics such as diflunisal, naproxol, paracetamol, salicylamide and salicyclic acid; antibiotics such as azidamphenicol, azithromycin, camptothecin, cefamandol, chloramphenicol, clarithromycin, clavulanic acid, clindamycin, demeclocyclin, doxycyclin, erythromycin, gentamycin, imipenem, latamoxef, metronidazole, neomycin, novobiocin, oleandomycin, oxytetracyclin, tetracycline, thiamenicol and tobramycin; antivirals such as acyclovir, d4C, ddC, DMDC, Fd4C, FddC, FMAU, FTC, 2'-fluoro-ara-dideoxyinosine, ganciclovir, lamivudine, penciclovir, SddC, stavudine, 5-trifluoromethyl-2'-deoxyuridine, zalcitabine and zidovudine; bisphosphonates such as EB-1053, etidronate, ibandronate, olpadronate, residronate, YH-529 and zolendronate; protease inhibitors such as ciprokiren, enalkiren, ritonavir, saquinavir and terlakiren; prostaglandins such as arbaprostil, carboprost, misoprostil and prostacydin; antidepressives such as 8-hydroxychlorimipramine and 2-hydroxyimipramine; antihypertonics such as sotarol and fenoldopam; anticholinergenics such as biperidine, procyclidin and trihexyphenidal; antiallergenics such as cromolyn; glucocorticoids such as betamethasone, budenosid, chlorprednison, clobetasol, clobetasone, corticosteron, cortisone, cortodexon, dexamethason, flucortolon, fludrocortisone, flumethasone, flunisolid, fluprednisolon, flurandrenolide, flurandrenolon acetonide, hydrocortisone, meprednisone, methylpresnisolon, paramethasone, prednisolon, prednisol, triamcinolon and triamcinolon acetonide; narcotic agonists and antagonists such as apomorphine, buprenorphine, butorphanol, codein, cyclazocin, hydromorphon, ketobemidon, levallorphan, levorphanol, metazocin, morphine, nalbuphin, nalmefen, naloxon, nalorphine, naltrexon, oxycodon, oxymorphon and pentazocin; stimulants such as mazindol and pseudoephidrine; anaesthetics such as hydroxydion and propofol; β-receptor blockers such as acebutolol, albuterol, alprenolol, atenolol, betazolol, bucindolol, cartelolol, celiprolol, cetamolol, labetalol, levobunelol, metoprolol, metipranolol, nadolol, oxyprenolol, pindolol, propanolol and timolol; α-sympathomimetics such as adrenalin, metaraminol, midodrin, norfenefrin, octapamine, oxedrin, oxilofrin, oximetazolin and phenylefrin; β-sympathomimetics such as bamethan, clenbuterol, fenoterol, hexoprenalin, isoprenalin, isoxsuprin, orciprenalin, reproterol, salbutamol and terbutalin; bronchodilators such as carbuterol, dyphillin, etophyllin, fenoterol, pirbuterol, rimiterol and terbutalin; cardiotonics such as digitoxin, dobutamin, etilefrin and prenalterol; antimycotics such as amphotericin B, chlorphenesin, nystatin and perimycin; anticoagulants such as acenocoumarol, dicoumarol, phenprocoumon and warfarin; vasodilators such as bamethan, dipyrimadol, diprophyllin, isoxsuprin, vincamin and xantinol nicotinate; antihypocholesteremics such as compactin, eptastatin, mevinolin and simvastatin; and miscellaneous drugs such as bromperidol (antipsychotic), dithranol (psoriasis) ergotamine (migraine) ivermectin (antihelminthic), metronidazole and secnizadole (antiprotozoals), nandrolon (anabolic), propafenon and quinadine (antiarythmics), quetiapine (CNS), serotonin (neurotransmitter) and silybin (hepatic disturbance).

In a preferred embodiment, drugs which contain hydroxyl groups (i.e., Y is —OR) include adenosine, cromolyn, cytarabine, decitabine, didanosine, docetaxel, gemcitabine, norgestrel, paclitaxel, pentostatin and vinblastine.

Examples of drugs which contain phosphonic acid or phosphonate moieties (i.e., Y is —P(O)(OR')R; and R' may be hydrogen) include, but are not limited to, adefovir, alendronate, AR-C69931MX, BMS-187745, ceronapril, CGP-24592, CGP-37849, CGP-39551, CGP-40116, cidofovir, clodronate, EB-1053, etidronate, fanapanel, foscarnet, fosfomycin, fosinopril, fosinoprilat, ibandronate, midafotel, neridronate, olpadronate, pamidronate, residronate, tenofovir, tiludronate, WAY-126090, YH-529 and zolendronate.

In a preferred embodiment, drugs which contain phosphonic acid or phosphonate moieties (i.e., Y is —P(O)(OR)R') include alendronate, cidofovir, clodronate, foscarnet, ibandronate, midafotel, olpadronate, pamidronate, residronate and zoledronate.

Examples of drugs which contain phosphoric acid or phosphate moieties (i.e., Y is —P(O)(OR)(OR'); and R' may be hydrogen) include, but are not limited to, bucladesine, choline alfoscerate, citocoline, fludarabine phosphate, fosopamine, GP-668, perifosine, triciribine phosphate and phosphate derivatives of nucleoside analogs which require phophorylation for activity, such as 3TC, acyclovir, AZT, BVDU, ddC, ddI, FMAU, FTC, ganciclovir, gemcitabine, H2G, lamivudine, penciclovir and the like.

In a preferred embodiment, drugs which contain phosphoric acid or phosphate moieties (i.e., Y is —P(O)(OR)(OR')) include bucladesine, choline alfoscerate, citocoline, fludarabine phosphate, fosopamine, GP-668, perfosine and triciribine.

The above examples of drug compounds are merely representative rather than comprehensive. Accordingly, given the teachings above, the skilled artisan may be able to identify drug molecules other than those listed above which may be converted to a 1-acyl-alkyl derivative.

Preferably, the compounds of structural Formula (I) have the structure of Formulae (IV) and (V), illustrated below. Here, Y is —NRR' and HNRR' is

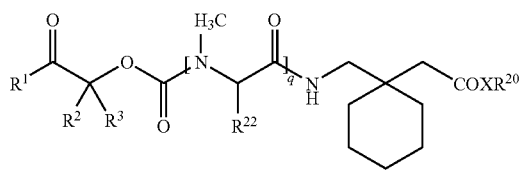

(IV)

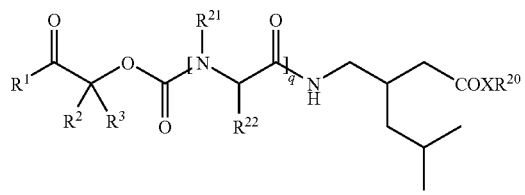

(V)

gabapentin and esters or thioesters thereof or pregabalin and esters or thioesters thereof. In Formulae (IV) and (V), X is O or S and $R^{20}$ is hydrogen, alkyl, substituted alkyl, aryl, substituted aryl, aryl alkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl, while q, $R^1$, $R^2$, $R^3$, $R^{21}$ and $R^{22}$ are as previously defined.

In one embodiment of compounds of Formulae (IV) and (V), $R^{20}$ is selected from the group consisting of hydrogen, alkyl, substituted alkyl aryl, substituted aryl, arylalkanyl, substituted arylalkanyl, cycloalkanyl, substituted cycloalkanyl, cycloheteroalkanyl and substituted cycloheteroalkanyl. In a preferred embodiment, X is O aid $R^{20}$ is hydrogen. In still another embodiment, X is O and $R^{20}$ is alkanyl, substituted alkanyl, alkenyl, substituted alkenyl, aryl or substituted aryl. Preferably, $R^{20}$ is —C(CH$_3$)=CH$_2$, —CH$_2$C(=O)N(CH$_3$)$_2$, 4-fluorophenyl or

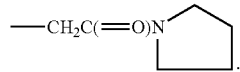

In one preferred embodiment of Formulae (IV) and (V), q is 0. In another preferred embodiment of Formulae (IV) and (V), q is 1.

In another embodiment of compounds of structural Formulae (IV) and (V), $R^{21}$ is hydrogen or alkyl. Preferably, $R^{21}$ is hydrogen, methyl, ethyl, propyl or butyl, more preferably, $R^{21}$ is hydrogen or methyl.

In still another embodiment of compounds of Formulae (IV) and (V), $R^{22}$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl or optionally, $R^{22}$ together with the carbon atom to which it is attached, the adjacent nitrogen atom and $R^{21}$ substituent form a cycloheteroalkyl or substituted cycloheteroalkyl ring. Preferably, $R^{22}$ is hydrogen, alkanyl, substituted alkanyl, aryl, substituted aryl, arylalkanyl, substituted arylalkanyl, cycloalkanyl, heteroarylalkyl and substituted heteroarylalkanyl or optionally, $R^{22}$ together with the carbon atom to which it is attached, the adjacent nitrogen atom and $R^{21}$ substituent form a cycloheteroalkyl or substituted cycloheteroalkyl ring.

In still another embodiment of compounds of Formulae (IV) and (V), $R^{22}$ together with the carbon atom to which it is attached, the adjacent nitrogen atom and $R^{21}$ substituent form a five membered ring. In another embodiment, R is hydrogen, cycloalkanyl or alkanyl. Preferably, $R^{22}$ is hydrogen, methyl, 2-propyl, 2-butyl, isobutyl, t-butyl, cyclopentyl or cyclohexyl.

In still another embodiment of compounds of Formulae (IV) and (V), $R^{22}$ is substituted alkanyl. Preferably, $R^{22}$ is —CH$_{20}$H, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, CH$_2$SH, —CH$_2$(CH$_2$)$_3$NH$_2$ or —CH$_2$CH$_2$CH$_2$NHC(NH)NH$_2$ In still another embodiment of compounds of Formulae (IV) and (V), $R^{22}$ is selected from the group consisting of aryl, arylalkanyl, substituted arylalkanyl and heteroarylalkanyl. Preferably, $R^{22}$ is phenyl, benzyl, 4-hydroxybenzyl, 2-imidazolyl or 2-indolyl.

In still another embodiment of compounds of Formulae (IV) and (V), q is 1, $R^{21}$ is hydrogen and $R^{22}$ is phenyl, benzyl, 4-hydroxybenzyl, 2-imidazolyl, 2-indolyl, CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, CH$_2$SH, —CH$_2$(CH$_2$)$_3$NH$_2$, —CH$_2$CH$_2$CH$_2$NHC(NH)NH$_2$, hydrogen, methyl, 2-propyl, 2-butyl, isobutyl, or $R^{22}$ together with the carbon atom to which it is attached, the adjacent nitrogen atom and $R^{21}$ substituent forrn a five membered ring.

In still another embodiment of compounds of Formulae (IV) and (V), $R^2$ and $R^3$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl or substituted heteroaryl. Preferably, $R^2$ and $R^3$ are independently hydrogen, alkyl, alkoxycarbonyl, aryl, arylalkyl, carbamoyl, cycloalkoxycarbonyl or heteroaryl. Preferably, when $R^2$ is alkoxycarbonyl, cycloalkoxycarbonyl or carbamoyl then $R^3$ is methyl. More preferably, $R^2$ and $R^3$ are independently hydrogen, methyl, ethyl, propyl, isopropyl, butyl, isobutyl, sec-butyl, tert-butyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclohexyloxycarbonyl, phenyl, benzyl, phenethyl or 3-pyridyl.

In still another embodiment of compounds of Formulae (IV) and (V), $R^2$ and $R^3$ are independently hydrogen, alkanyl or substituted alkanyl. Preferably, $R^2$ and $R^3$ are hydrogen or alkanyl. More preferably, $R^2$ and $R^3$ are independently hydrogen, methyl, ethyl, propyl, isopropyl or butyl.

In still another embodiment of compounds of Formulae (IV) and (V), $R^2$ and $R^3$ are independently hydrogen, aryl, arylalkyl or heteroaryl. Preferably, $R^2$ and $R^3$ are independently, phenyl, benzyl, phenethyl or 3-pyridyl. More preferably, $R^2$ is hydrogen and $R^3$ is hydrogen; $R^2$ is methyl and $R^3$ is hydrogen; $R^2$ is ethyl and $R^3$ is hydrogen; $R^2$ is propyl and $R^3$ is hydrogen; $R^2$ is isopropyl and $R^3$ is hydrogen; $R^2$ is butyl and $R^3$ is hydrogen; $R^2$ is phenyl and $R^3$ is hydrogen; $R^2$ is methoxycarbonyl and $R^3$ is methyl; $R^2$ is ethoxycarbonyl and $R^3$ is methyl; $R^2$ is isopropoxycarbonyl and $R^3$ is methyl; $R^2$ is methyl and $R^3$ is methyl.

In still another embodiment of compounds of Formulae (IV) and (V), $R^1$ is hydrogen, alkyl, substituted alkyl, aryl, substituted aryl, arylalkyl, substituted arylalkyl, cycloalkyl, substituted cycloalkyl, heteroaryl, substituted heteroaryl or a $C_{23}$ bile acid moiety. Preferably, $R^1$ is hydrogen, alkyl, substituted alkyl, aryl, arylalkyl, cycloalkyl or heteroaryl. More preferably, $R^1$ is methyl, ethyl, propyl, isopropyl, butyl, isobutyl, sec-butyl, tert-butyl, pentyl, isopentyl, sec-pentyl, neopentyl, cyclobutyl, cyclopentyl, cyclohexyl, phenyl, 4-methoxyphenyl, benzyl, phenethyl, styryl or 3-pyridyl.

In still another embodiment of compounds of Formulae (IV) and (V), $R^1$ is alkanyl or substituted alkanyl or a $C_{23}$ bile acid moiety. Preferably, $R^1$ is methyl, ethyl, propyl, isopropyl, butyl, isobutyl, sec-butyl, tert-butyl, pentyl, isopentyl, sec-pentyl or neopentyl. More preferably, $R^1$ is hydrogen, methyl, ethyl, propyl, isopropyl or butyl.

In still another embodiment of compounds of Formulae (IV) and (V), $R^1$ is cycloalkyl or substituted cycloalkyl. Preferably, $R^1$ is cyclobutyl, cyclopentyl or cyclohexyl.

In still another embodiment of compounds of Formulae (IV) and (V), $R^1$ is hydrogen, aryl, arylalkyl or heteroaryl. Preferably, $R^1$ is phenyl, 4-methoxyphenyl, benzyl, phenethyl, styryl or 3-pyridyl.

In still another embodiment of compounds of Formulae (IV) and (V), $R^1$ is methyl, ethyl, propyl, isopropyl, butyl, isobutyl, sec-butyl, tert-butyl, cyclobutyl, cyclopentyl, cyclohexyl, phenyl, benzyl or 3-pyridyl, $R^2$ is hydrogen and $R^3$ is hydrogen. In still another embodiment, $R^1$ is methyl, ethyl, propyl, isopropyl, butyl, isobutyl, sec-butyl, tert-butyl, cyclobutyl, cyclopentyl, cyclohexyl, phenyl, benzyl or 3-pyridyl, $R^2$ is methyl and $R^3$ is hydrogen. In still another embodiment, $R^1$ is methyl, ethyl, propyl, isopropyl, butyl, isobutyl, sec-butyl, tert-butyl, cyclobutyl, cyclopentyl, cyclohexyl, phenyl, benzyl or 3-pyridyl, $R^2$ is ethyl and $R^3$ is hydrogen. In still another embodiment, $R^1$ is methyl, ethyl, propyl, isopropyl, butyl, isobutyl, sec-butyl, tert-butyl, cyclobutyl, cyclopentyl, cyclohexyl, phenyl, benzyl or 3-pyridyl, $R^2$ is propyl and $R^3$ is hydrogen. In still another embodiment, $R^1$ is methyl, ethyl, propyl, isopropyl, butyl, isobutyl, sec-butyl, tert-butyl, cyclobutyl, cyclopentyl, cyclohexyl, phenyl, benzyl or 3-pyridyl, $R^2$ is isopropyl and $R^3$ is hydrogen. In still another embodiment, $R^1$ is methyl, ethyl, propyl, isopropyl, butyl, isobutyl, sec-butyl, tert-butyl, cyclobutyl, cyclopentyl, cyclohexyl, phenyl, benzyl or 3-pyridyl, $R^2$ is butyl and $R^3$ is hydrogen. In still another embodiment, $R^1$ is methyl, ethyl, propyl, isopropyl, butyl, isobutyl, sec-butyl, tert-butyl, cyclobutyl, cyclopentyl, cyclohexyl, phenyl, benzyl or 3-pyridyl, $R^2$ is isobutyl and $R^3$ is hydrogen. In still another embodiment, $R^1$ is methyl, ethyl, propyl, isopropyl, butyl, isobutyl, sec-butyl, tert-butyl, cyclobutyl, cyclopentyl, cyclohexyl, phenyl, benzyl or 3-pyridyl, $R^2$ is sec-butyl and $R^3$ is hydrogen. In still another embodiment, $R^1$ is methyl, ethyl, propyl, isopropyl, butyl, isobutyl, sec-butyl, tert-butyl, cyclobutyl, cyclopentyl, cyclohexyl, phenyl, benzyl or 3-pyridyl, $R^2$ is tert-butyl and $R^3$ is hydrogen. In still another embodiment, $R^1$ is methyl, ethyl, propyl, isopropyl, butyl, isobutyl, sec-butyl, tert-butyl, cyclobutyl, cyclopentyl, cyclohexyl, phenyl, benzyl or 3-pyridyl, $R^2$ is phenyl and $R^3$ is hydrogen.

In still another embodiment of compounds of Formulae (IV) and (V), $R^1$ is methyl, ethyl, propyl, isopropyl, butyl, isobutyl, sec-butyl, tert-butyl, cyclobutyl, cyclopentyl, cyclohexyl, phenyl, benzyl or 3-pyridyl, $R^2$ is methyl and $R^3$ is methyl. In still another embodiment, $R^1$ is methyl, ethyl, propyl, isopropyl, butyl, isobutyl, sec-butyl, tert-butyl, cyclobutyl, cyclopentyl, cyclohexyl, phenyl, benzyl or 3-pyridyl, $R^2$ is methoxycarbonyl and $R^3$ is methyl. In still another embodiment, $R^1$ is methyl, ethyl, propyl, isopropyl, butyl, isobutyl, sec-butyl, tert-butyl, cyclobutyl, cyclopentyl, cyclohexyl, phenyl, benzyl or 3-pyridyl, $R^2$ is ethoxycarbonyl and $R^3$ is methyl. In still another embodiment, $R^1$ is methyl, ethyl, propyl, isopropyl, butyl, isobutyl, sec-butyl, tert-butyl, cyclobutyl, cyclopentyl, cyclohexyl, phenyl, benzyl or 3-pyridyl, $R^2$ is isopropoxycarbonyl and $R^3$ is methyl. In still another embodiment, $R^1$ is methyl, ethyl, propyl, isopropyl, butyl, isobutyl, sec-butyl, tert-butyl, cyclobutyl, cyclopentyl, cyclohexyl, phenyl, benzyl or 3-pyridyl, $R^2$ is cyclohexyloxycarbonyl and $R^3$ is methyl.

In still another embodiment of compounds of Formulae (IV) and (V), $R^1$ is methyl, ethyl, propyl, isopropyl, butyl, isobutyl, sec-butyl, tert-butyl, cyclobutyl, cyclopentyl, cyclohexyl, phenyl, benzyl or 3-pyridyl and $R^2$ and $R^3$ together with the atom to which they are attached form a cyclohexyl ring. In still another embodiment, $R^1$ and $R^2$ form a cyclobutyl ring, a cyclopentyl ring or cyclohexyl ring and $R^3$ is hydrogen. In still another embodiment, $R^1$ and $R^2$ form a cyclobutyl ring, a cyclopentyl ring or cyclohexyl ring and $R^3$ is methyl.

In still another embodiment of compounds of Formulae (IV) and (V), q is 0 or 1.

4.3 Synthesis of the Compounds of the Invention

The compounds of the invention may be obtained via the synthetic methods illustrated in Schemes 1-7. Starting materials useful for preparing compounds of the invention and intermediates thereof (i.e., α-hydroxy ketones) are commercially available or can be prepared by well-known synthetic methods (See, e.g., *Tetrahedron Lett.* 1990, 31, 2599; *Tetrahedron Lett.* 1997, 31, 7183). Other methods for synthesis of the compounds described herein and/or starting materials are either described in the art or will be readily apparent to the skilled artisan in view of general references well-known in the art (See e.g., Green et al., "Protective Groups in Organic Chemistry", (Wiley, 2$^{nd}$ ed. 1991); Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995) and may be used to synthesize the compounds of the invention. Accordingly, the methods presented in the Schemes herein are illustrative rather than comprehensive.

Reaction of hydroxyketone 101 (either commercially available or prepared by procedures known to the skilled artisan) as illustrated in Scheme 1 and drug derivatives such as isocyanate 103, halofornate 105 (or synthetic equivalent such as a p-nitrophenyl carbonate derivative), acid halide 107 (or synthetic equivalent such as anhydrides of carboxylic acids, active esters, etc.), phosphonyl halide 109 (or synthetic equivalent such as active esters) or phosphoryl halide 111 (or synthetic equivalent such as active esters) provides ketocarbamate 134, ketocarbonate 115, ketoester 117, ketophosphonate 119 or ketophosphate 121, respectively. Methods for preparing the drug derivatives (i.e., derivatives 103, 105, 107, 109 and 111) and procedures for converting the reactants to products are well-known to the skilled artisan.

Scheme 1

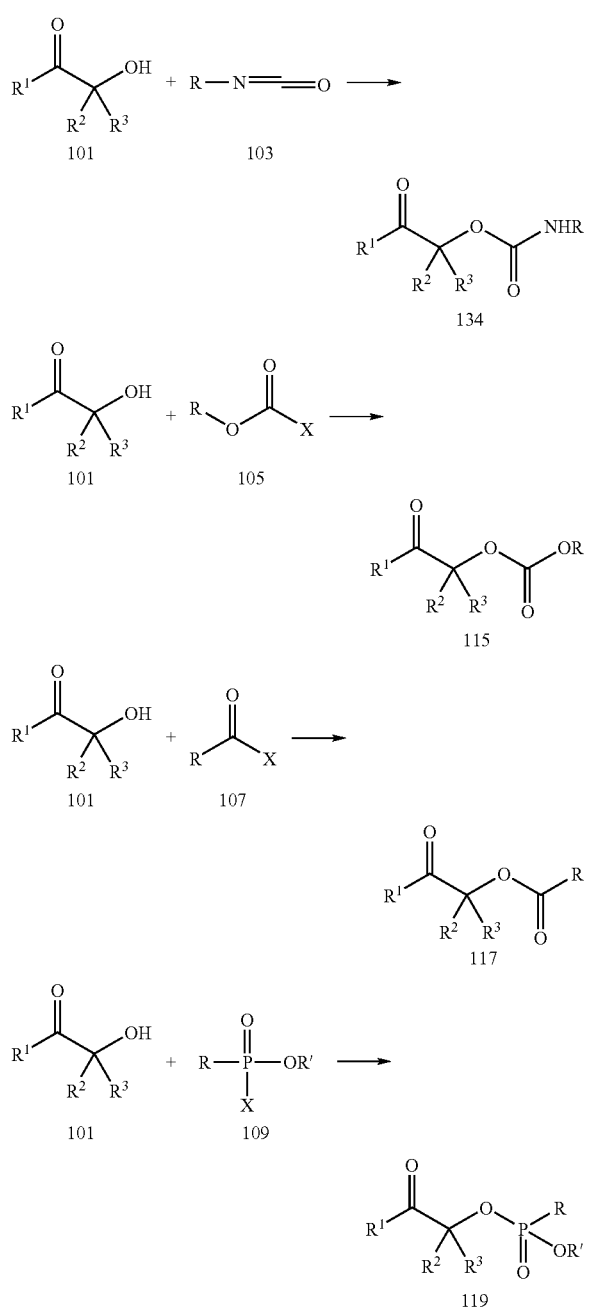

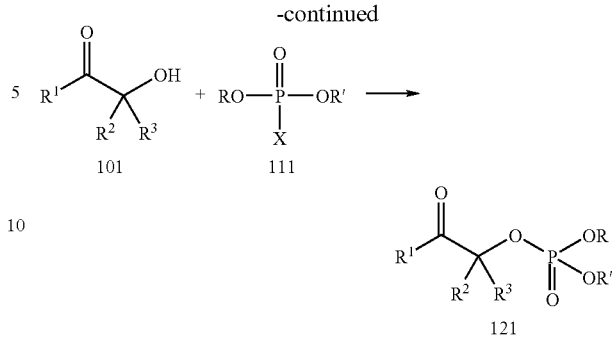

Another procedure for synthesizing compounds 117, 119 and 121 is illustrated in Scheme 2.

Scheme 2

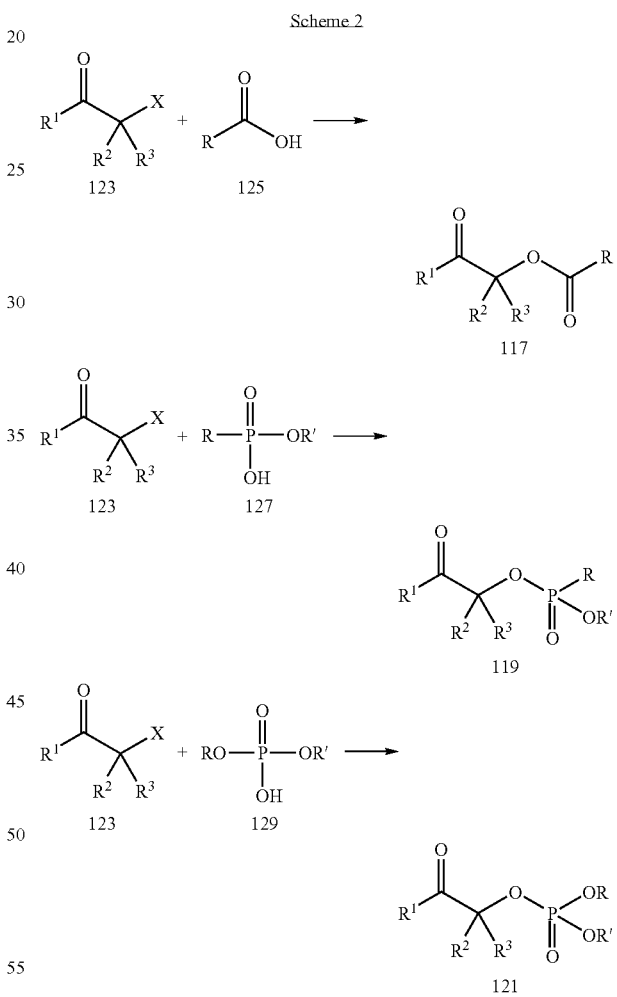

Haloketone 123, (X=halide, preferably either $R^2$ or $R^3$ is hydrogen) which may be prepared by methods known to the skilled artisan, may be reacted with drugs such as carboxylic acid 125, phosphonate 127 or phosphate 129 to provide ketoester 117, ketophosphonate 119 and ketophosphate 121, respectively. Preferably, the reactions illustrated above are conducted in the presence of base (e.g., cesium carbonate, silver carbonate or silver oxide) in an appropriate solvent (e.g., dimethylformamide or hexamethyphosphoramide).

Other procedures for effecting the transformations illustrated above will be apparent to those of skill in the art.

Another method, which is analogous to the processes depicted in Scheme 2, is illustrated in Scheme 3. Amine drug 131 may be carbonylated to provide carbamic acid 133 which may be reacted with haloketone 123 in the presence of base (e.g., cesium carbonate, silver carbonate or silver oxide) in an appropriate solvent (e.g., dimethylformamide or hexamethyphosphoramide) to yield ketocarbamate 113.

Scheme 3

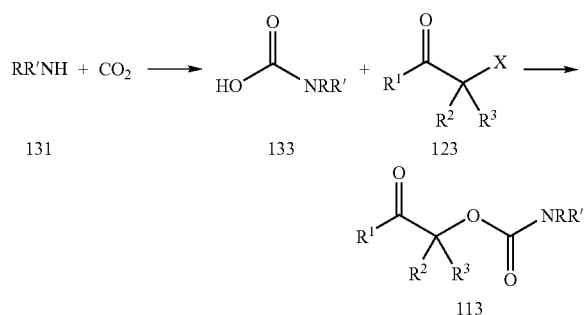

Another method, which may used to synthesize ketocarbamate 113 and ketocarbonate 115, is illustrated in Scheme 4. Hydroxyketone 101 may be reacted with phosgene or sythetic equivalent 135 (e.g., triphosgene, carbonyldiimidazole, p-nitrophenylchloroformate, etc.) to provide activated derivative 136 (Y=leaving group), which upon treatment with alcohol drug 137 or amine drug 131 is converted to ketocarbonate 115 or ketocarbamate 113, respectively.

Scheme 4

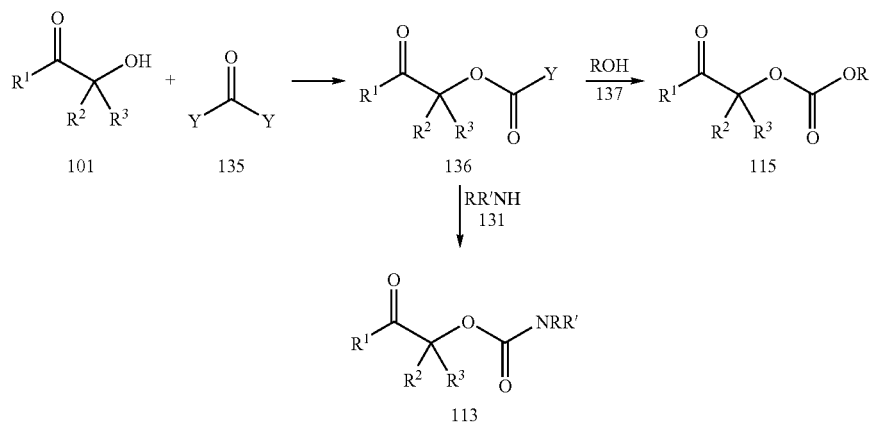

Propargylic alcohol derivatives may be used to synthesize ketocarbamate 146, ketocarbonate 148, ketoester 150, ketophosphonate 152 or ketophosphate 154. Illustrated in Scheme 5, and well-known to those of the skill in the art, nucleophilic addition of alkynyl organomettalic reagent 139 to aldehyde or ketone 141 provides propargylic alcohol 143.

Scheme 5

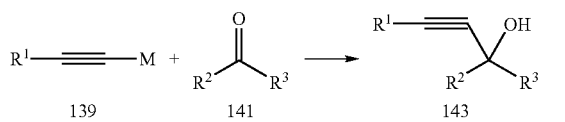

As illustrated in Scheme 6, propargylic alcohol 143 may be converted to propargylic carbamate 145, propargylic carbonate 147, propargylic ester 149, propargylic phosphonate 151 or propargylic phosphate 153 using, for example, the methods shown in Scheme 1 or Scheme 4. Propargylic carbamate 145, propargylic carbonate 147, propargylic ester 149, propargylic phosphonate 151 or propargylic phosphate 153 may be transformed to ketocarbamate 146, ketocarbonate 148, ketoester 150, ketophosphonate 152 or ketophosphate 154, respectively, for example, by oxymercuration (e.g., HgO or HgSO$_4$ in the presence of water).

Scheme 6

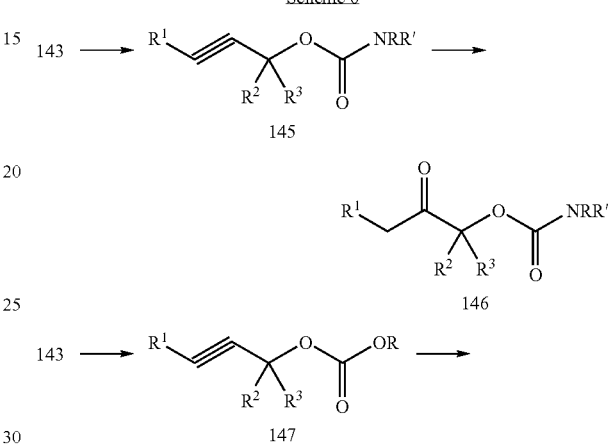

-continued

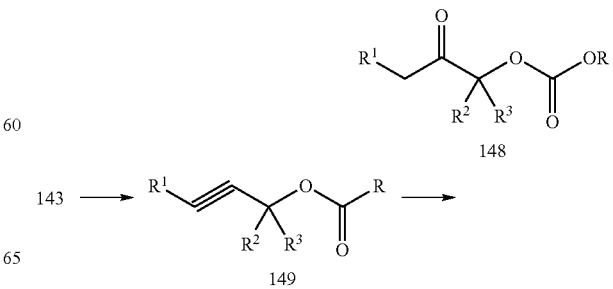

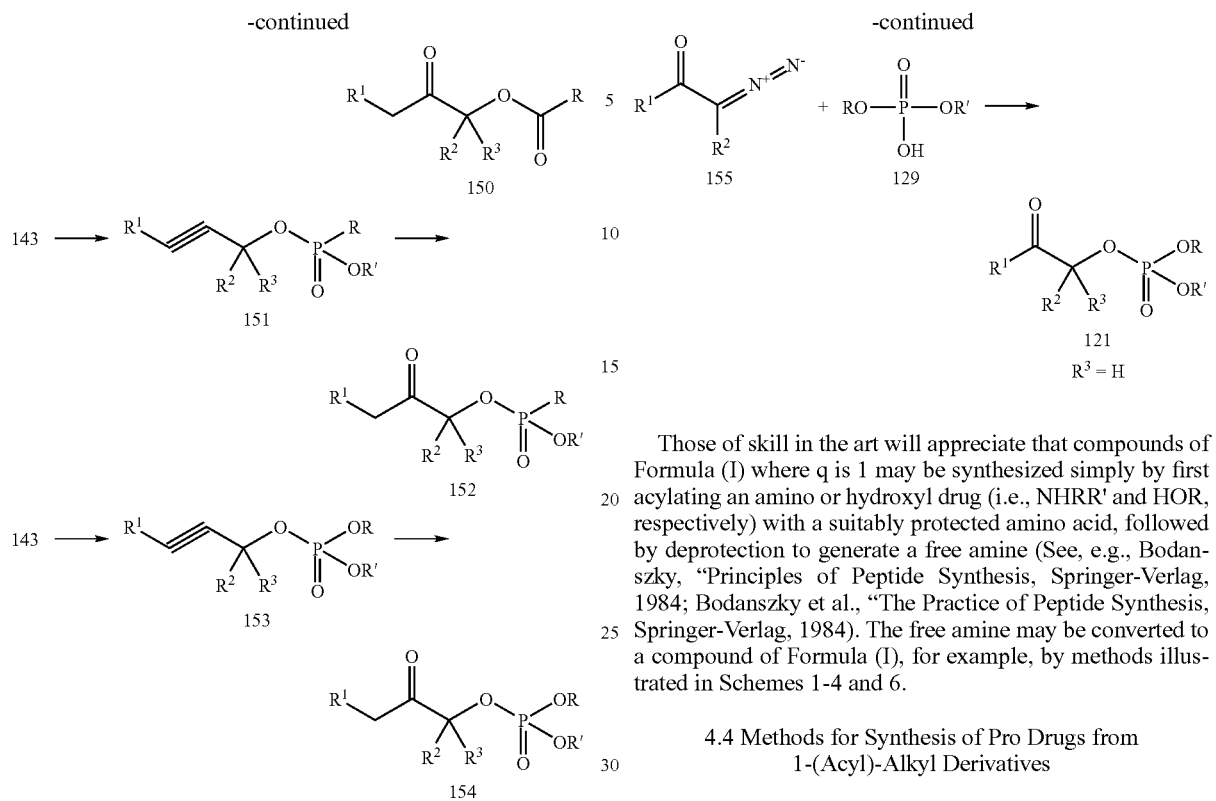

As illustrated in Scheme 7, diazoketone 155 may be reacted with carboxylic acid 125, phoshonate 127 or phosphate 129 to provide ketoester 117, ketophosphonate 119 or ketophosonate 121, respectively ($R^3$ is hydrogen in Scheme 7, below). Preferably, the reaction illustrated above is carried out in the presence of a metal catalyst (e.g., $Rh_2(OAc)_4$).

Scheme 7

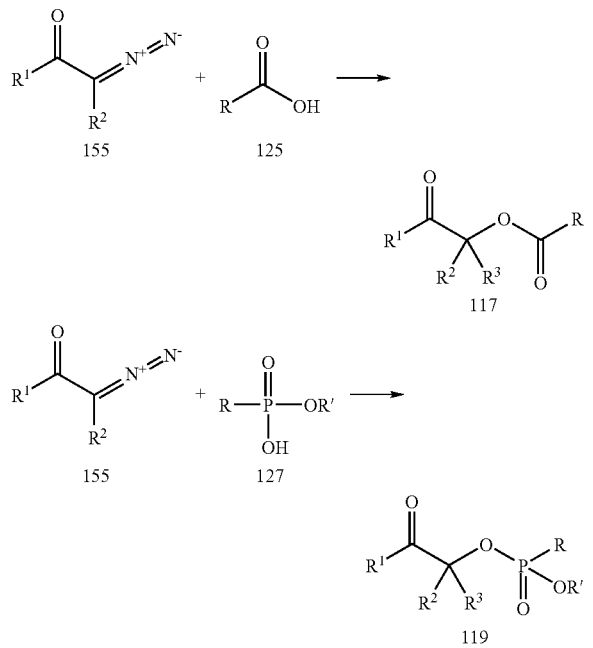

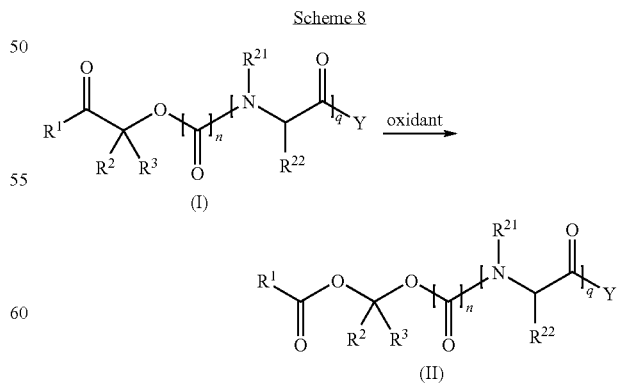

Those of skill in the art will appreciate that compounds of Formula (I) where q is 1 may be synthesized simply by first acylating an amino or hydroxyl drug (i.e., NHRR' and HOR, respectively) with a suitably protected amino acid, followed by deprotection to generate a free amine (See, e.g., Bodanszky, "Principles of Peptide Synthesis, Springer-Verlag, 1984; Bodanszky et al., "The Practice of Peptide Synthesis, Springer-Verlag, 1984). The free amine may be converted to a compound of Formula (I), for example, by methods illustrated in Schemes 1-4 and 6.

4.4 Methods for Synthesis of Pro Drugs from 1-(Acyl)-Alkyl Derivatives

Generally, the present invention provides methods for synthesis of 1-(acyloxy)-alkyl derivatives. Preferably, 1-(acyloxy)-alkyl derivatives are synthesized by oxidation of 1-acyl-alkyl derivatives. More preferably, 1-(acyloxy)-alkyl derivatives of pharmacologically effective drugs are synthesized by oxidation of 1-acyl-alkyl derivatives of pharmacologically effective drugs.

In a preferred embodiment, the method of the current invention oxidizes a 1-acyl-alkyl derivative of structural Formula (I) to a 1-(acyloxy)-alkyl derivative of structural Formula (II), as shown in Scheme 8 below, where $R^1$, $R^2$, $R^3$, $R^{21}$, $R^{22}$, Y, q and n are defined as described in Section 4.2, herein. Preferred embodiments of $R^1$, $R^2$, $R^3$, $R^{21}$, $R^{22}$, Y, q and n for compounds of structural Formula (I) and structural Formula (II) individually or in combination, are also described in Section 4.2, herein.

Particularly preferred 1-(acyloxy)-alkyl derivatives include 1-acyl-alkoxycarbonyl derivatives of gabapentin, esters and thioesters thereof or pregabalin, esters and thioesters thereof in Formulae (VI) and (VII) respectively, where $R^1$, $R^2$, $R^3$, $R^{20}$, $R^{21}$, $R^{22}$, Y, X, q and n are defined as described in Section 4.2, herein.

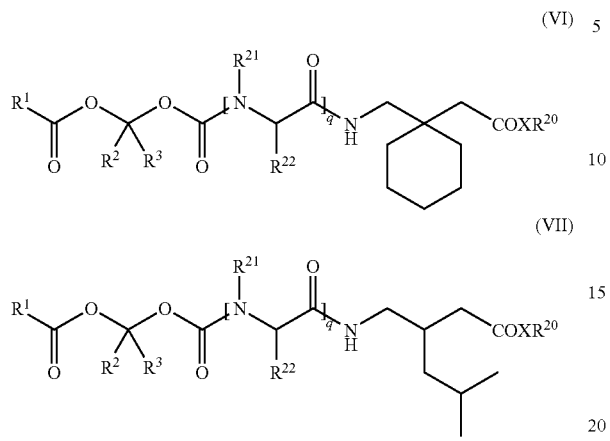

Preferred embodiments of $R^1$, $R^2$, $R^3$, $R^{20}$, $R^{21}$, $R^{22}$, Y, X, q and n, individually or in combination for compounds of Formulae (VI) or (VII) have also been described in Section 4.2, herein.

Preferably, the oxidation of a compound of structural Formula (I) to a compound of structural Formula (II) is performed in the liquid phase, more preferably, in the presence of a solvent. Choosing a solvent for oxidation of a compound of structural Formula (I) is well within the ambit of one of skill in the art. Generally, a preferred solvent will dissolve, at least partially, both the oxidant and the compound of structural Formula (I) and will be inert to the reaction conditions. Preferred solvents include, but are not limited to, t-butanol, diethylether, acetic acid, hexane, dichloroethane, dichloromethane, ethyl acetate, acetonitrile, methanol, chloroform and water. As is obvious to the skilled artisan, mixtures of the above solvents may also be used in the oxidation of a compound of structural Formula (I) to a compound of structural Formula (II).

Generally, an oxidant may be an organism (e.g., yeast or bacteria), or a chemical reagent (e.g., an enzyme or peroxide) which can convert a compound of structural Formula (I) to a compound of structural Formula (II). Preferred oxidants include those, which have been successfully used in Baeyer-Villager oxidations of ketones to esters or lactones (Strukul, *Angnew. Chem. Int. Ed.*, 1998, 37, 1198; Renz et al., *Eur. J. Org. Chem.* 1999, 737; Beller et al., in "Transitions Metals in Organic Synthesis" Chapter 2, Wiley VCH; Stewart, *Current Organic Chemistry*, 1998, 2, 195; Kayser et al., *Synlett*, 1999, 1, 153).

In one embodiment, the oxidant is yeast (e.g., *Saccharomyces cerevisiae*) or bacteria (e.g., *Acinetobacter* sp. NCIB 9871). In another embodiment, the oxidant is a peroxide (preferably, $H_2O_2$, t-BuOOH or $(TMS)_2O_2$) or a peroxyacid (preferably, $CF_3CO_3H$, $MeCO_3H$, mCPBA, monopernaleic acid, mono-o-perphthalic acid, 3,5 dinitroperbenzoic acid, o-nitroperbenzoic acid, m-nitroperbenzoic acid, p-nitroperbenzoic acid, performic acid, perbenzoic acid, persulfuric acid, or a salt thereof). In still another embodiment, the oxidant is an enzyme and oxygen. Preferably, the enzyme is cyclohexanone monooxygenase.

In a preferred embodiment, a transition metal complex may be contacted with a peroxide or peroxy acid prior to reaction with a compound of Formula (1). Preferably, the transition metal complexes include, but are not limited, to those illustrated below:

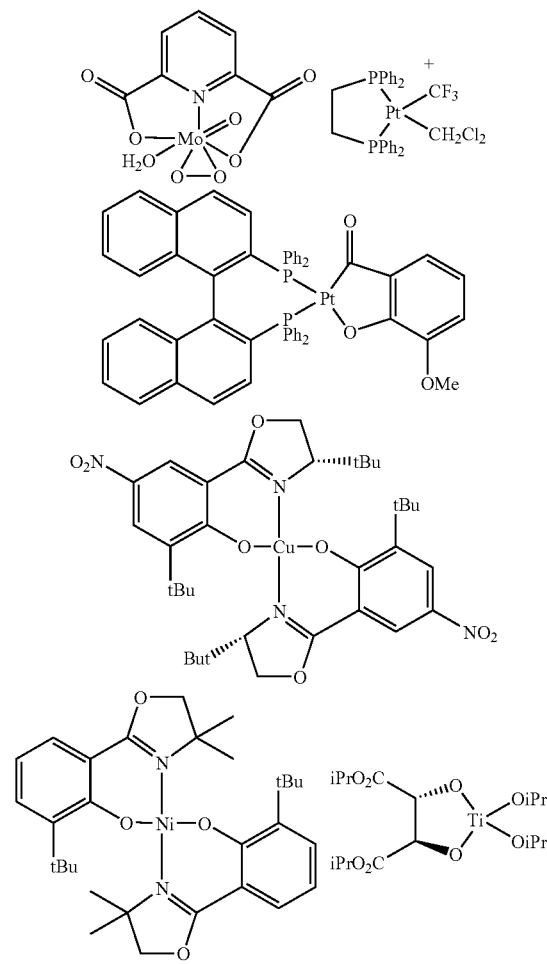

While not wishing to be bound by theory, the transition metal complex may react with the peroxide or peroxy acid to form a new oxidant, which may be more active than the parent oxidant.

Further, the use of additives in the oxidation of a compound of structural Formula (I) to a compound of structural Formula (II) is also contemplated. While not wishing to be bound by theory, additives may either catalyze the reaction or stabilize the final product or both.

Preferably the molar ratio of oxidant to the compound of Formula (I) is between 8:1 and 1:1. More preferably the molar ratio of oxidant to the compound of Formula (I) is between 4:1 and 1:1. Even more preferably the molar ratio of oxidant to the compound of Formula (I) is between 2:1 and 1:1. Still more preferably, when the oxidant is perbenzoic acid or a substituted perbenzoic acid, the molar ratio of oxidant to the compound of Formula (I) is ~2:1. The entire quantity of oxidant may either be added to the compound of Formula (I) in one portion or in several portions. Typically, when a large excess of oxidant is used relative to the compound of Formula (I), the oxidant is added in several portions.

In a preferred embodiment, a Lewis acid or a protic acid or any combination of Lewis acid or protic acid may be used in the oxidation of a compound of structural Formula (I) (preferably, in the presence of a solvent). Preferred Lewis acids include, but are not limited to, $BF_3$, $SeO_2$, $MeReO_3$, $MnO_2$, $SnCl_4$, $Sc(OTf)_3$, $Ti(O-iPr)_4$, $Al_2O_3$ and $Fe_2O_3$.

Preferred protic acids include, but are not limited to, acetic acid, p-toluenesulfonic acid, methanesulfonic acid, trifluoroacetic acid, trifluoromethanesulfonic acid, hydrochloric acid and sulfuric acid. While not wishing to be bound by theory, the Lewis acid and/or protic acid may catalyze oxidation by increasing the electrophilicity of the carbonyl group in structural Formula (I).

In another preferred embodiment, the oxidation may be conducted in the presence of a base, which is preferably a buffer. Preferred bases include, but are not limited to, $Na_2HPO_4$, $K_2HPO_4$, $NaHCO_3$, $Na_2CO_3$ and $Li_2CO_3$. While not wishing to be bound by theory, the base may stabilize acid sensitive products by reacting with acidic by-products formed during oxidation.

Generally, the temperature of the oxidation may be readily optimized by methods known to those of ordinary skill in the art. Preferably, the oxidation of a compound of Formula (I) is carried out at a temperature between about −25° C. and about 120° C. (more preferably, between about 0° C. and about 25° C.).

A particularly advantageous feature of this method of synthesis of 1-(acyloxy)-alkyl derivatives (II) is that the oxidation of 1-acyl-alkyl derivatives (I) proceeds stereospecifically, with retention of configuration at the carbon atom initially adjacent to the carbonyl group in hydroxyketone (I). This may be exploited in a non-racemic synthesis of 1-(acyloxy)-alkyl prodrug derivatives, as illustrated in Scheme 9 with the synthesis of 1-{[(α-(S)-isobutanoyloxyisobutoxy)carbonyl]-aminomethyl}-1-cyclohexane acetic acid and 1-{[(α-(R)-isobutanoyloxyisobutoxy)-carbonyl]aminomethyl}-1-cyclohexane acetic acid, 181 and 183. In this synthesis the chiral building blocks (S)-2-hydroxy-3-methylbutyric acid 157 and (R)-2-hydroxy-3-methylbutyric acid 159 are converted to the chiral α-hydroxyketones 173 and 175 respectively. Activation of these synthons as their p-nitrophenyl carbonates and reaction with gabapentin affords the carbamates 177 and 179. Oxidation with mCPBA provides the enantiomeric acyloxyalkylcarbamate prodrugs 181 and 183.

Scheme 9

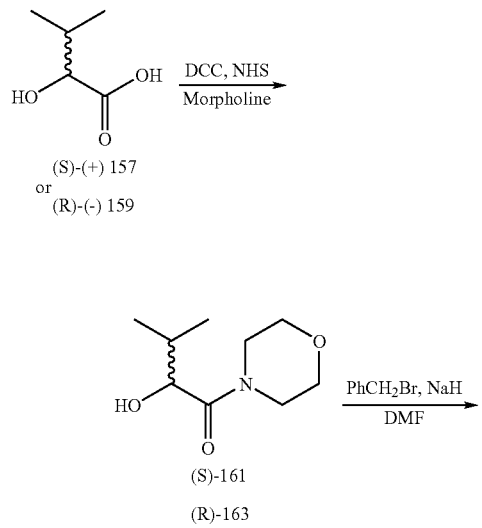

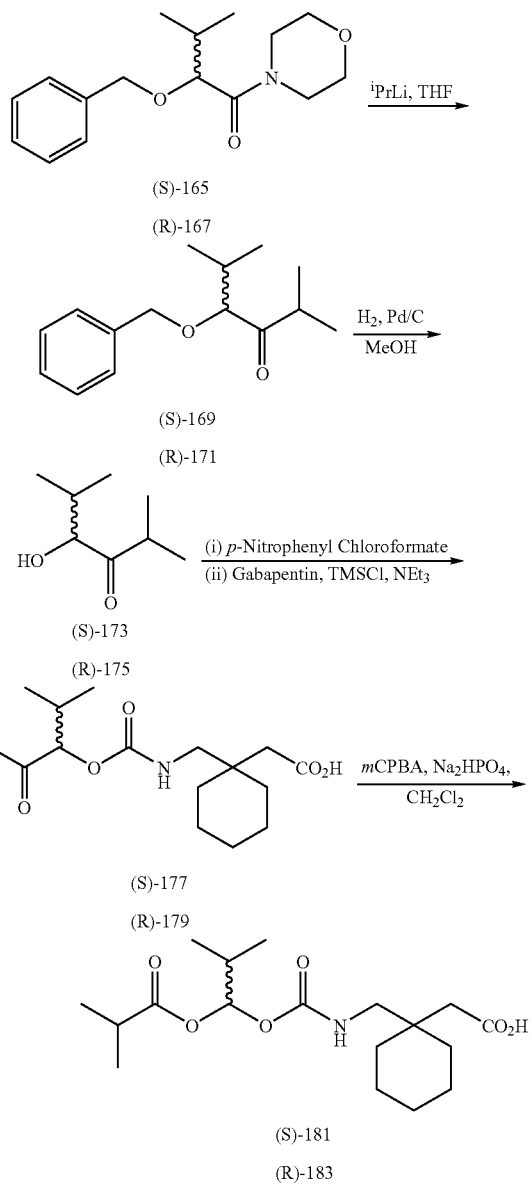

4.5 Therapeutic Uses of Compounds of Structural Formulae (IV), (V), (VI) and (VII)

In accordance with the invention, a compound and/or a composition containing a compound of structural Formulae (IV), (V), (VI) or (VII) is administered to a patient, preferably a human, suffering from epilepsy, depression, anxiety, psychosis, faintness attacks, hypokinesia, cranial disorders, neurodegenerative disorders, panic, pain (especially, neuropathic pain and muscular and skeletal pain), inflammatory disease (ie., arthritis), insomnia, gastrointestinal disorders or ethanol withdrawal syndrome. Further, in certain embodiments, the compounds and/or compositions of the invention are administered to a patient, preferably a human, as a preventative measure against various diseases or disorders. Thus, the compounds and/or compositions containing compound(s) of structural Formulae (IV), (V), (VI) or (VII) may be administered as a preventative measure to a patient having a predisposition for epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders and ethanol withdrawal syndrome. Accordingly, the compounds and/or compositions containing compound(s) of structural Formulae (IV), (V), (VI) or (VII) be used for the prevention of one disease or disorder and concurrently treating another (e.g., prevention of psychosis while treating gastrointestinal disorders; prevention of neuropathic pain while treating ethanol withdrawal syndrome).

The suitability of the compounds and/or compositions containing compound(s) of structural Formulae (IV), (V), (VI) or (VII) in treating epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders and ethanol withdrawal syndrome may be determined by methods described in the art (See, e.g., Satzinger et al., U.S. Pat. No. 4,024,175; Satzinger et al., U.S. Pat. No. 4,087,544; Woodruff, U.S. Pat. No. 5,084,479; Silverman et al., U.S. Pat. No. 5,563,175; Singh, U.S. Pat. No. 6,001,876; Horwell et al., U.S. Pat. No. 6,020,370; Silverman et al., U.S. Pat. No. 6,028,214; Horwell et al., U.S. Pat. No. 6,103,932; Silverman et al., U.S. Pat. No. 6,117,906; Silverman, International Publication No. WO 92/09560; Silverman et al., International Publication No. WO 93/23383; Horwell et al., International Publication No. WO 97/29101, Horwell et al., International Publication No. WO 97/33858; Horwell et al., International Publication No. WO 97/33859; Bryans et al., International Publication No. WO 98/17627; Guglietta et al., International Publication No. WO 99/08671; Bryans et al., International Publication No. WO 99/21824; Bryans et al., International Publication No. WO 99/31057; Magnus-Miller et al., International Publication No. WO 99/37296; Bryans et al., International Publication No. WO 99/31075; Bryans et al., International Publication No. WO 99/61424; Pande, International Publication No. WO 00/23067; Bryans, International Publication No. WO 00/31020; Bryans et al., International Publication No. WO 00/50027; Bryans et al, International Publication No. WO 02/00209; Gallop et al., U.S. patent application Ser. No. 10/171,485). The compounds and/or compositions of the invention may be used to treat epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders and ethanol withdrawal syndrome y procedures described in the art (see references above). Thus, those of skill in the art may readily assay and use the compounds and/or compositions containing compound(s) of structural Formulae (IV), (V), (VI) or (VII) to treat epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders and ethanol withdrawal syndrome.

4.6 Therapeutic/Prophylactic Administration

The compounds, and/or compositions containing compound(s), of structural Formulae (IV), (V), (VI) or (VII) may be advantageously used in human medicine. As previously described in Section 4.5 above, compounds and compositions containing compound(s) of structural Formulae (IV), (V), (VI) or (VII) are useful for the treatment or prevention of epilepsy, depression, anxiety, psychosis, faintness attacks, hypokinesia, cranial disorders, neurodegenerative disorders, panic, pain (especially, neuropathic pain and muscular and skeletal pain), inflammatory disease (i.e., arthritis), insomnia, gastrointestinal disorders or ethanol withdrawal syndrome.

When used to treat or prevent the above disease or disorders compounds and/or compositions of the invention may be administered or applied singly, in combination with other agents. The compounds and/or compositions of the invention may also be administered or applied singly, in combination with other pharmaceutically active agents, including other compounds and/or compositions of the invention.

The current invention provides methods of treatment and prophylaxis by administration to a patient of a therapeutically effective amount of a composition and/or compound of the invention. The patient may be an animal, is more preferably a mammal, and most preferably a human.

The present compounds and/or compositions of the invention, which comprise one or more compounds and/or compositions of the invention are preferably administered orally. The compounds and/or compositions of the invention may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or composition of the invention. Methods of administration include, but are not limited to, intradermal, intramuscular, intraperitoneal, intravenous, subcutaneous, intranasal, epidural, oral, sublingual, intranasal, intracerebral, intravaginal, transdennal, rectally, by inhalation, or topically, particularly to the ears, nose, eyes, or skin.

In particularly preferred embodiments, the compounds and/or compositions of the invention can be delivered via sustained release systems, preferably oral sustained release systems. In one embodiment, a pump may be used (See, Langer, supra; Sefton, 1987, *CRC Crit. Ref Biomed. Eng.* 14:201; Saudek et al., 1989, *N. Engl. J. Med.* 321:574).

In another embodiment, polymeric materials can be used (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, N.Y. (1984); Ranger and Peppas, 1983, *J Macromol. Sci. Rev. Macromol Chem.* 23:61; see also Levy et al., 1985, *Science* 228: 190; During et al., 1989, *Ann. Neurol.* 25:351; Howard et al, 1989, *J. Neurosurg.* 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethers have been described (Alderman, *Int. J. Pharm. Tech. & Prod. Mfr.,* 1984, 5(3) 1-9). Factors affecting drug release are well known to the skilled artisan and have been described in the art (Bamba et al., *Int. J. Pharm.,* 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still another embodiment, osmotic delivery systems are used for oral sustained release administration (Verma et al., *Drug Dev. Ind. Pharm.*, 2000, 26:695-708). In a preferred embodiment, OROS® osmotic delivery systems sold by Alza Corporation of Mountain View, Calif. are used for oral sustained release delivery devices (See for example, Theeuwes et al., U.S. Pat. No. 3,845,770; and Theeuwes et al., U.S. Pat. No. 3,916,899).

In yet another embodiment, a controlled-release system can be placed in proximity of the target of the compounds and/or composition of the invention, thus requiring only a fraction of the systemic dose (See, e.g., Goodson, in "Medical Applications of Controlled Release," supra, vol. 2, pp. 115-138 (1984)). Other controlled-release systems discussed in Langer, 1990, *Science* 249:1527-1533 may also be used.

The compounds, and/or compositions containing compound(s) of structural Formulae (IV), (V), (VI) or (VII) preferably provide GABA analogs (e.g., gabapentin and pregablin) upon in vivo administration to a patient. While not wishing to bound by theory, the promoiety or promoieties of the compounds and/or compositions of the invention may be cleaved either chemically and/or enzymatically. One or more enzymes present in the stomach, intestinal lumen, intestinal tissue, blood, liver, brain or any other suitable tissue of a mammal may enzymatically cleave the promoiety or promoieties of the compounds and/or compositions of the invention. The mechanism of cleavage is not important to the current invention. Preferably, GABA analogs formed by cleavage of prodrugs from the compounds of the invention do not contain substantial quantities of lactam contaminant (preferably, less than 0.5% by weight, more preferably, less than 0.2% by weight, most preferably less than 0.1% by weight). The extent of release of lactam contaminant from the prodrugs of this invention may be assessed using the standard in vitro analytical methods.

While not wishing to bound by theory, the promoiety or promoieties of the compounds of structural Formulae (IV), (V), (VI) or (VII) may be cleaved prior to absorption by the gastrointestinal tract (e.g., within the stomach or intestinal lumen) and/or after absorption by the gastrointestinal tract (e.g., in intestinal tissue, blood, liver or other suitable tissue of a mammal). If the promoiety or promoieties of the compounds and/or compositions of the invention are cleaved prior to absorption by the gastrointestinal tract, the resulting GABA analogs may be absorbed into the systemic circulation conventionally (e.g., via the large neutral amino acid transporter located in the small intestine). If the promoiety or promoieties of the compounds of the invention are cleaved after absorption by the gastrointestinal tract, these GABA analog prodrugs may have the opportunity to be absorbed into the systemic circulation either by passive diffusion, active transport or by both passive and active processes.

If the promoiety or promoieties of the compounds of structural Formulae (IV), (V), (VI) or (VII) are cleaved after absorption by the gastrointestinal tract, these GABA analog prodrugs may have the opportunity to be absorbed into the systemic circulation from the large intestine. In this situation, the compounds and/or compositions of the invention are preferably administered as sustained release systems. In a preferred embodiment, the compounds and/or compositions of the invention are delivered by oral sustained release administration. Preferably, in this embodiment, the compounds and/or compositions of the invention are administered twice per day (more preferably, once per day).

4.7 Compositions of the Invention

The present compositions contain a therapeutically effective amount of one or more compounds of the invention, preferably in purified form, together with a suitable amount of a pharmaceutically acceptable vehicle, which so as to provide the form for proper administration to a patient. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents. In addition, auxiliary, stabilizing, thickening, lubricating and coloring agents may be used.

In one embodiment, the compositions of the invention containing compound(s) of structural Formulae (IV), (V), (VI) or (VII) are free of lactam side products formed by intramolecular cyclization. In a preferred embodiment, the compositions of the invention are stable to extended storage (preferably, greater than one year) without substantial lactam formation (preferably, less than 0.5% lactam by weight, more preferably, less than 0.2% lactam by weight, most preferably, less than 0.1% lactam by weight).

Pharmaceutical compositions comprising a compound of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the invention into preparations which can be used pharmaceutically. Proper formulation is dependent upon the route of administration chosen.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 17th Edition, 1985). Preferred compositions of the invention are formulated for oral delivery, particularly for oral sustained release administration.

Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry coloring agents and preserving agents, to provide a pharmaceutically palatable preparation. Moreover, where in tablet or pill form, the compositions may be coated to delay disintegration and absorption in the gastrointestinal tract, thereby providing a sustained action over an extended period of time. Selectively permeable membranes surrounding an osmotically active driving compound are also suitable. for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM) etc. Additionally, flavoring agents, preservatives, coloring agents, bile salts, acylcamitines and the like may be added.

Compositions for administration via other routes may. also be contemplated. For buccal administration, the compositions may take the form of tablets, lozenges, etc. formulated in conventional manner. Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611). A compound of the invention may also be formulated in rectal or vaginal compositions such as suppositories or retention enemas, e.g., containing conventional suppository bases such as cocoa butter or other glycerides. In addition to the formulations described previously, a compound of the invention may also be formulated as a depot preparation. Such long acting formulations may be administered by implantation (for example, subcutaneously or intramuscularly) or by intramuscular injection. Thus, for example, a compound of the invention may be formulated with suitable polymeric or hydrophobic materials (for example, as an emulsion in an acceptable oil) or ion exchange resins, or as sparingly soluble derivatives, for example, as a sparingly soluble salt.

When a compound of the invention is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

4.8 Methods of Use and Doses

A compound of the invention, or compositions thereof, will generally be used in an amount effective to achieve the intended purpose. For use to treat or prevent diseases or disorders such as epilepsy, depression, anxiety, psychosis, faintness attacks, hypokinesia, cranial disorders, neurodegenerative disorders, panic, pain (especially neuropathic pain and muscular and skeletal pain), inflammatory disease (i.e., arthritis), insomnia, gastrointestinal disorders or ethanol withdrawal syndrome the compounds of Formulae (IV), (V), (VI) or (VI), and compositions containing a compound of Formulae (IV), (V), (VI) or (VI), are administered or applied in a therapeutically effective amount.

The amount of a compound of the invention that will be effective in the treatment of a particular disorder or condition disclosed herein will depend on the nature of the disorder or condition, and can be determined by standard clinical techniques known in the art as previously described. In addition, in vitro or in vivo assays may optionally be employed to help identify optimal dosage ranges. The amount of a compound of the invention administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In a preferred embodiment, the compounds of the invention are delivered by oral sustained release administration. Preferably, in this embodiment, the compounds of the invention are administered twice per day (more preferably, once per day). Dosing may be repeated intermittently, may be provided alone or in combination with other drugs and may continue as long as required for effective treatment of the disease state or disorder.

In the case of GABA analog prodrugs, suitable dosage ranges for oral administration are dependent on the potency of the parent GABA analog drug, but are generally about 0.001 mg to about 200 mg of a compound of the invention per kilogram body weight. When the GABA analog is gabapentin, typical daily doses of the parent drug in adult patients are 900 mg/day to 3600 mg/day and the dose of gabapentin prodrug may be adjusted to provide an equivalent molar quantity of gabapentin. Other GABA analogs may be more potent than gabapentin (e.g., pregabalin), and lower doses may be appropriate for both the parent drug and any prodrug (measured on an equivalent molar basis). Dosage ranges may be readily determined by methods known to the skilled artisan.

The compounds of the invention are preferably assayed in vitro and in vivo, for the desired therapeutic or prophylactic activity, prior to use in humans. For example, in the case of a GABA analog used to treat convulsions, in vitro assays can be used to determine whether administration of a specific compound of Formulae (IV), (V), (VI) or (VI), or a combination thereof, is preferred for reducing convulsion. The compounds of the invention may also be demonstrated to be effective and safe using animal model systems.

Preferably, a therapeutically effective dose of a compound of the invention described herein will provide therapeutic benefit without causing substantial toxicity. Toxicity of compounds of the invention may be determined using standard pharmaceutical procedures and may be readily ascertained by the skilled artisan. The dose ratio between toxic and therapeutic effect is the therapeutic index. A compound of the invention will preferably exhibit particularly high therapeutic indices in treating disease and disorders. The dosage of a compound of the inventions described herein will preferably be within a range of circulating concentrations that include an effective dose with little or no toxicity.

4.9. Combination Therapy

In certain embodiments of the present invention, the compounds of the invention can be used in combination therapy with at least one other therapeutic agent. The compound of the invention and the therapeutic agent can act additively or, more preferably, synergistically. In a preferred embodiment, a composition comprising a compound of the invention is administered concurrently with the administration of another therapeutic agent, which can be part of the same composition as the compound of the invention or a different composition. In another embodiment, a composition comprising a compound of the invention is administered prior or subsequent to administration of another therapeutic agent.

5. EXAMPLES

The invention is further defined by reference to the following examples, which describe in detail, preparation of compounds of the invention illustrate methods of synthesizing 1-(acyloxy)-alkyl derivatives from 1-acyl-alkyl derivatives. It will be apparent to those skilled in the art that many modifications, both to materials and methods, may be practiced without departing from the scope of the invention.

In the examples below, the following abbreviations have the following meanings. If an abbreviation is not defined, it has its generally accepted meaning.

| | |
|---|---|
| Atm = | atmosphere |
| Boc = | tert-butyloxycarbonyl |
| Cbz = | carbobenzyloxy |
| DCC = | dicyclohexylcarbodiimide |
| DMAP = | 4-N,N-dimethylaminopyridine |
| DMF = | N,N-dimethylformamide |
| DMSO = | dimethylsulfoxide |
| Fmoc = | 9-fluorenylmethyloxycarbonyl |
| g = | gram |
| h = | hour |
| HPLC = | high pressure liquid chromatography |
| L = | liter |
| LC/MS = | liquid chromatography/mass spectroscopy |
| M = | molar |
| m-CPBA = | meta-chloroperbenzoic acid |
| min = | minute |
| mL = | milliliter |
| mmol = | millimoles |
| NHS = | N-hydroxysuccinimide |
| PBS = | phosphate buffered saline |
| THF = | tetrahydrofuran |
| TFA = | trifluoroacetic acid |
| TLC = | thin layer chromatography |
| TMS = | trimethylsilyl |
| μL = | microliter |
| μM = | micromolar |
| v/v = | volume to volume |

5.1 Example 1

1-{[(α-Benzoyloxybenzyloxy)carbonyl]aminomethyl}-1-Cyclohexane Acetic Acid (1)

Step A: 1,1-Cyclohexanediacetic Anhydride (3)

A suspension of 1,1-cyclohexanediacetic acid (39.95 mmol) in acetic anhydride (159.8 mmol) was refluxed gently until a clear solution was obtained (ca. 1 h). The reaction mixture was kept at reflux for another hour until the reaction was complete. The reaction mixture was cooled to room temperature and acetic acid and excess acetic anhydride were removed under vacuum to afford 7.28 g (100%) of (3). $^1$H NMR (CDCl$_3$): 2.65 (4H, s); 1.54-1.43 (10H, m).

Step B: 1-[(2-Cyanoethoxycarbonyl)methyl]-1-Cyclohexane Acetic Acid (5)

8.2 mL of 1.6M butyllithium was added to a −78° C. solution of 3-hydroxy-propionitrile (13.19 mmol) in 50 mL of THF. The reaction mixture was warmed to 30° C. and stirred for 30 minutes. Then, a solution of 1,1-cyclohexanediacetic anhydride (10.99 mmol) in 10 mL of THF was added dropwise. The reaction mixture was warmed to room temperature over a period of one hour and stirred at room temperature with monitoring by TLC. When the reaction was judged complete, the reaction mixture was quenched with saturated ammonium chloride solution and THF was removed under reduced pressure. The aqueous layer was extracted with ethyl acetate, washed with brine and dried over Na$_2$SO$_4$. After concentration in vacuo the residue was purified on silica gel (5% methanol in dichloromethane) to afford 2.64 g (95%) of the title compound. $^1$H NMR (CDCl$_3$): δ 4.28 (2H, t, J=6.4 Hz); 2.71 (2H, t, J=6.4 Hz); 2.61 (4H, m); 1.52-1.42 (10H, m).

Step C: 2-Cyanoethyl 1-isocyanatomethyl-1-Cyclohexane Acetate (7)

1.5 mL of N-methyl morpholine (13.62 mmol) and 1.3 mL of ethyl chloroformate (13.03 mmol) was added to a solution of 1-[(2-cyanoethoxycarbonyl)-methyl]-1-cyclohexane acetic acid (5) (11.84 mmol) in 30 mL of anhydrous THF at −20° C. under nitrogen atmosphere. The reaction mixture was stirred at −20° C. for 20 minutes, warmed to −5° C., an aqueous solution of NaN$_3$ (29.61 mmol, in 3.5 mL of H$_2$O) was added and then stirred for 30 minutes at −5° C. to −10° C. Then, THF was removed under reduced pressure and the residue was extracted with CH$_2$Cl$_2$ and dried over Na$_2$SO$_4$. After concentration in vacuo the crude product was dissolved in 20 mL of anhydrous toluene and refluxed for 20 minutes. The mixture was cooled to room temperature and toluene was removed under reduced pressure. The residue was purified on silica gel (15% ethyl acetate in hexane) to afford 1.9 g (64%) of the title compound. $^1$H NMR (CDCl$_3$): δ 4.29 (2H, t, J=6.0 Hz); 3.42 (2H, s); 2.73 (2H, t, J=6.0 Hz); 2.44 (2H, s); 1.49-1.39 (10H, m).

Step D: 2-Cyanoethyl 1-{[(α-Benzoylbenzyloxy) carbonyl]aminomethyl}-1-Cyclohexane Acetate (9)

A solution of benzoin (0.599 mmol) and 2-cyanoethyl 1-isocyanatomethyl-1-cyclohexane acetate (7) (0.599 mmol) in 10 mL of anhydrous toluene was refluxed overnight. The reaction mixture was concentrated and the residue purified on silica gel (40% ethyl acetate in hexane) to afford 230 mg (83%) of the title compound. $^1$H NMR (CDCl$_3$): δ 7.95 (2H, dd, J=8.2, 1.4 Hz); 7.50-7.46 (3H, m); 7.41 (5H, m); 6.84 (1H, s); 5.40 (1H, t, J=6.8 Hz); 4.26 (2H, m); 3.24 (2H, d, J=6.8 Hz); 2.68 (2H, dt, J=2.4, 6.4 Hz); 2.36 (2H, d, J=1.2 Hz); 1.52-1.37 (10H, m).

Step E: 2-Cyanoethyl 1-{[(α-Benzoyloxybenzyloxy) carbonyl]aminomethyl}-1-Cyclohexane Acetate (11)

A solution of 2-cyanoethyl 1-{[(α-benzoylbenzyloxy)carbonyl]aminomethyl}-1-cyclohexane acetate (9) (115 mg, 0.248 mmol) in 4 mL of $CH_2Cl_2$ was added to a mixture of mCPBA (77%, 111 mg, 0.497 mmol) and $Na_2CO_3$ (52.7 mg, 0.497 mmol) at room temperature. The resulting suspension was stirred at room temperature with TLC monitoring. After completion of the reaction (about 8 hours) the reaction mixture was diluted with $CH_2Cl_2$, washed with saturated $NaHCO_3$ solution and brine and dried over $Na_2SO_4$. After concentration in vacuo the residue was purified on silica gel (40% ethyl acetate in hexane) to afford 89 mg (75%) of the title compound. $^1H$ NMR ($CDCl_3$): δ 8.08 (2H, dd, J=6.8, 1.6 Hz); 7.91 (1H, s); 7.63-7.54 (3H, m); 7.44-7.40 (5H, m); 5.42 (1H, t, J=6.4 Hz); 4.22 (2H, t, J=6.2 Hz); 3.25 (2H, dd, J=6.4, 4.6 Hz); 2.65 (2H, t, J=6.2 Hz); 2.35 (2H, s); 1.53-1.37 (10H, m). $^{13}C$ NMR ($CDCl_3$): δ 172.11; 164.73; 154.75; 136.29; 133.70; 130.18; 129.85; 129.63; 128.85; 128.68; 126.85; 117.11; 91.41; 58.94; 47.93; 10.06; 38.09; 34.15; 26.00; 21.55; 18.16.

Step F: 1-{[(α-Benzoyloxybenzyloxy)carbonyl]aminomethyl}-1-Cyclohexane Acetic Acid (1)

DBU (79.2 mg, 78 μL, 0.520 mmol) was added to a solution of 2-cyanoethyl 1-{[(α-benzoyloxybenzyloxy)carbonyl]aminomethyl}-1-cyclohexane acetate (11) (166 mg, 0.347 mmol) in 10 mL of $CH_2Cl_2$ at −10° C. The reaction mixture was stirred at 0° C. for 1 hour, then allowed to warm to room temperature, stirred for two hours and cooled to 0° C. Another 78 μL of DBU was added, the reaction mixture was stirred for 3 hours at 0° C. and then allowed to warm to room temperature. The reaction mixture was diluted with $CH_2Cl_2$, washed with citric acid and brine and dried over $Na_2SO_4$. The solvent was removed under reduced pressure and the residue was purified by reversed phase HPLC to afford 7 mg (4.7%) of the title compound. M.p. 75.5-76.0° C. $^1H$ NMR ($CDCl_3$): δ 8.08 (2H, dd, J=8.8, 1.2 Hz); 7.89 (1H, s); 7.63-7.55 (3H, m); 7.46-7.26 (5H, m); 5.38 (1H, t, J=6.8 Hz); 3.26 (2H, dd, J=6.8, 0.8 Hz); 2.34 (2H, s); 1.58-1.35 (10 H, m). MS (ESI) m/z 424 $(M-H^{31})$.

5.2 Example 2

Alternative Method for Preparation of 1-{[(α-Benzoyloxybenzvloxy)carbonyl]aminomethyl}-1-Cyclohexane Acetic Acid (1)

Step A: p-Nitrophenyl aα-benzoylbenzylcarbonate (13)

A solution of benzoin (2.0 g, 9.42 mmol) in 60 mL of $CH_2Cl_2$ was treated with DMAP (1.21 g, 9.89 mmol) and p-nitrophenyl-chloroformate (1.99 g, 9.89 mmol) at room temperature. The reaction mixture was stirred for 3 hours at room temperature to afford the title compound, which was used in the next reaction without purification.

Step B: 1-{[(α-Benzoylbenzyloxy)carbonyl]aminomethyl}-1-Cyclohexane Acetic Acid (15)

To a suspension of gabapentin (1.70 g, 9.90 mmol) in $CH_2Cl_2$ at 0° C. was added triethylamine (2.76 mL, 19.81 mmol) and TMSCl (2.51 mL, 19.81 mmol). The reaction was then stirred for 30 min at room temperature. To this mixture was added compound (13) (prepared above) in $CH_2Cl_2$, and the resulting mixture was stirred at room temperature for 5 hrs. The reaction mixture was diluted with dichloromethane, washed with brine. The organic phase was dried over $Na_2SO_4$. The solvent was removed under vacuum and the residue was purified by chromatography on silica gel with 5% methanol in $CH_2Cl_2$ to 3.78 g (90% over two steps) of the title compound. $^1H$ NMR ($CDCl_3$): δ 7.93 (2H, dd, J=7.2 Hz); 7.50-7.33 (8H, m); 6.85 (1H, m); 5.58 (1H, t, J=6.8 Hz); 3.24 (2H, d, J=7.2 Hz); 2.30 (2H, s); 1.48-1.35 (10H, m).

Step C: 1-{[(α-Benzoyloxybenzyloxy)carbonyl]aminomethyl}-1-Cyclohexane Acetic Acid (1)

mCPBA (77%, 2.07 g, 9.24 mmol) and $NaHCO_3$ (0.78 g, 9.24 mmol) was added to a solution of 1-{[(α-benzoylbenzyloxy)carbonyl]aminomethyl}-1-cyclohexane acetic acid (15) (1.89 g, 4.62 mmol) in 40 mL of $CH_2Cl_2$ at room temperature and the resulting mixture was stirred at room temperature overnight. The reaction mixture was acidified with citric acid, extracted with $CH_2Cl_2$ and the organic phase was washed with brine, dried over $Na_2SO_4$ and concentrated under reduced pressure. The residue was purified by reverse phase preparative HPLC to afford 960 mg (49%) of the title compound.

5.3 Example 3

1-{[(α-Benzoyloxyethoxy)carbonyl]aminomethyl}-1-Cyclohexane Acetic Acid (17)

Following the procedure of Example 2, and substituting 2-hydroxy-1-phenyl-1-propanone for benzoin, provided 5 mg of the title compound (17). $^1H$ NMR ($CDCl_3$, 400 MHz): δ 1.44-1.36 (m, 10H), 1.62 (d, J=5.6 Hz, 3H), 2.34 (s, 2H), 3.24 (d, J=6.8 Hz, 2H), 5.28 (t, J=6.8 Hz, 1H), 7.06 (q. J=5.6 Hz, 1H), 7.44 (m, 2H), 7.56 (m, 1H), 8.03 (dd, J=8.4, 1.6 Hz, 2H).

5.4 Example 4

1-{[(α-Benzoyloxy-2-phenylethoxy)carbonyl]aminomethyl}-1-Cyclohexane Acetic Acid (19)

Step A: 2-Phenyl-[1,3]-dithiane (21)

To a solution of benzaldehyde (10.6 g, 100 mmol) and 1,3-propane dithiol in $CH_2Cl_2$ (150 mL) at room temperature was dropwise added $BF_3.Et_2O$ (6.3 mL, 50 mmol) and the resulting mixture was stirred at room temperature for 2 hours. The reaction mixture was then diluted with $CH_2Cl_2$, filtered and the filtrate washed with brine, saturated $NaHCO_3$, brine and dried over $Na_2SO_4$. The solvent was removed under reduced pressure to afford a white solid, which was recrystallized from a 1:1 mixture of ether and hexane to afford 17.0 g (87%) of the title compound (21) as white crystalline needles. $^1H$ NMR ($CDCl_3$, 400 MHz): δ 1.91 (m, 1H), 2.14 (m, 1H), 2.89 (m, 2H), 3.04 (m, 2H), 5.16 (s, 1H), 7.35-7.28 (m, 3H), 7.46 (m, 2H).

Step B: 2-Phenyl-1-(2-phenyl-[1,3]-dithian-2-yl)-ethanol (23)

To a solution of 2-phenyl-[1,3]-dithiane (21) (4.0 g, 20.4 mmol) in THF at −30° C. was added a 1.6 M solution of n-butyllithium in THF (15.3 mL, 24.4 mmol). After stirring for 30 minutes at −30° C., a solution of phenylacetylaldehyde (2.45 g, 20.4 mmol) in tetrahydrofuran was added dropwise at −30° C. The resulting reaction mixture was stirred for another hour at 0° C. The reaction was quenched with saturated $NH_4Cl$ solution and extracted with ethyl acetate. The combined organic extracts were washed with saturated $NH_4Cl$ solution, brine and dried over Na$_2$SO$_4$. After filtrating and concentrating, the crude product was purified by flash chromatography on silica gel, (25% ethyl acetate in hexanes), to afford 2.63 g (71%) of the title compound (23). $^1$H NMR (CDCl$_3$, 400 MHz): δ 1.97 (m, 2H), 2.23 (dd, J=4.0, 1.2 Hz, 1H), 2.43 (dd, J=13.6, 10.2 Hz, 1H), 2.77 (m, 4H), 3.02 (d, J=13.6 Hz, 1H), 4.07 (m, 1H), 7.44-7.13 (m, 8H), 8.02 (dd, J=8.4, 1.4 Hz, 2H).

Step C: 2-Hydroxy-1,3-diphenyl-propan-1-one (25)

To a solution of 2-phenyl-1-(2-phenyl-[1,3]-dithian-2-yl)-ethanol (23) (2.50 g, 7.9 mmol) in 100 mL of a 9:1 mixture of acetonitrile and water was added mercuric perchlorate hydrate (4.1 g, 10.3 mmol). The resulting mixture was stirred at room temperature for 5 minutes and thin layer chromatography indicated that the reaction was completed. The mixture was diluted with ethyl acetate, filtered through a pad of Celite and the filtrate was washed with saturated NaHCO$_3$, brine and dried over Na$_2$SO$_4$. The solvent was removed under reduced pressure and the crude product was purified by flash chromatography on silica gel, (20% ethyl acetate in hexanes) to afford 1.32 g (74%) of the title compound (25). $^1$H NMR (CDCl$_3$, 400 MHz): δ 2.90 (dd, J=14.4, 7.0 Hz, 1H), 3.20 (dd, J=14.4, 4.0 Hz, 1H), 3.70 (d, J=6.8 Hz, 1H), 5.35 (m, 1H), 7.28-7.11 (m, 5H), 7.53 (m, 2H), 7.65 (m, 1H), 7.93 (d, J=7.2 Hz, 2H).

Step D: 1-{[(α-Benzoyloxy-2-phenylethoxy)carbonyl]aminomethyl}-1-Cyclohexane Acetic Acid (19)

Following the procedure of Example 2, and substituting 2-hydroxy-1,3-diphenyl-propan-1-one for benzoin, provided 181 mg of the title compound (19). $^1$H NMR (CDCl$_3$, 400 MHz): δ 1.45-1.29 (m, 10H), 2.24 (d, J=13.6 Hz, 1H), 2.28 (d, J=13.6Hz, 1H), 3.22 (m, 4H), 5.26 (t, J=6.6 Hz, 1H), 7.16 (t, J=5.6 Hz, 1H), 7.33-7.25 (m, 5H), 7.40 (m, 2H), 7.57 (m, 1H), 8.02 (m, 2H).

5.5 Example 5

1-{[(α-(3-Methylbutanoyloxy)-2-phenylethoxy)carbonyl]aminomethyl}-1-Cyclohexane Acetic Acid (27)

Following the procedure of Example 4 and substituting 3-methylbutyraldehyde for benzaldehyde in Step A, provided 95 mg of the title compound (27). $^1$H NMR (CDCl$_3$, 400 MHz): δ 0.88-0.90 (m, 6H), 1.16-1.29 (m, 10H), 2.06 (m, 1H), 2.16 (m, 2H), 2.26 (m, 2H), 3.08 (d, J=6.8 Hz, 2H), 3.19 (m, 2H), 5.22 (t, J=6.8 Hz, 1H), 6.93(t, J=6 Hz, 1H), 7.31-7.23 (m, 5H).

5.6 Example 6

1-{[(α-Benzoyloxybutoxy)carbonyl]aminomethyl}-1-Cyclohexane Acetic Acid (29)

Following the procedure of Example 4 and substituting butyraldehyde for phenylacetaldehyde in Step B, provided 240 mg of the title compound (29). $^1$H NMR (CDCl$_3$, 400 MHz): δ 0.99 (t, J=7.6 Hz, 3H), 1.52-1.38 (m, 12H), 1.89 (m, 2H), 2.31 (s, 2H), 3.24 (m, 2H), 5.34 (t, J=6.6 Hz, 1H), 6.70 (t, J=5.6 Hz, 1H), 7.42 (m, 2H), 7.56 (m, 1H), 8.04 (m, 2H).

5.7 Example 7

1-{[(α-Acetoxybutoxy)carbonyl]aminomethyl}-1-Cyclohexane Acetic Acid (31)

Following the procedure of Example 4, and substituting acetaldehyde for benzaldehyde in Step A and substituting butyraldehyde for phenylacetaldehyde in Step B respectively, provided 42 mg of the title compound (31). $^1$H NMR (CD$_3$OD, 400 MHz): δ 0.95 (m, 3H), 1.52-1.31 (m,12H), 1.72 (m, 2H), 2.02 (s, 3H), 2.27 (s, 2H), 3.20 (s, 2H), 6.67 (t, J=5.6 Hz, 1H).

5.8 Example 8

1-{[(α-Butanoyloxybutoxy)carbonyl]aminomethyl}-1-Cyclohexane Acetic Acid (33)

Following the procedure of Example 2, and substituting butyroin for benzoin, provided 210 mg of the title compound (33). $^1$H NMR (CDCl$_3$, 400 MHz); δ 0.93 (m, 6H), 1.37-1.76 (m, 16H), 2.30 (m, 4H), 3.23 (m, 2H), 5.25 (broad triplet, 1H), 6.73 (m, 1H). MS (ESI) m/z 356.45 (M−H)$^+$.

5.9 Example 9

1-{[(α-Acetoxybenzyloxy)carbonyl]aminomethyl}-1-Cyclohexane Acetic Acid (35)

Following the procedure of Example 2, and substituting 1-hydroxy-1-phenyl-propan-2-one for benzoin, provided the title compound (35). $^1$H NMR (CDCl$_3$): δ 7.40 (5H, m); 5.95 (1H, s); 5.58 (1H, t, J=6.8 Hz); 3.25 (2H, d, J=6.8 Hz); 2.34 (2H, s); 2.11 (3H, s); 1.50-1.38 (10H, m).

5.10 Example 10

1-{[(α-Isobutanoyloxybutoxy)carbonyl]aminomethyl}-1-Cyclohexane Acetic Acid (37)

Step A: 2-Isopropyl-1,3-Dithiane (39)

To a mixture of isobutyraldehyde (9.1 mL, 100 mmol) and 1,3-propanedithiol (10 mL, 100 mmol) in dichloromethane at 0° C. was added boron trifluoride diethyl etherate (6.4 mL, 50 mmol). The resulting mixture was stirred at 0° C. for 30 min and at room temperature for 30 min. The reaction mixture was washed with brine, 5% NaHCO$_3$, and brine again. The organic phase was separated and dried over Na$_2$SO$_4$, then concentrated to give 16 g (100%) of the title compound as a yellow liquid. This was carried to the next step without further purification. $^1$H NMR (CDCl$_3$, 400 MHz): δ 1.057 (d, J=7.2 Hz, 3H), 1.059 (d, J=7.2 Hz, 3H), 1.80 (m, 1H), 1.97-2.08 (m, 2H), 2.82 (m, 4H), 4.00 (d, J=5.2 Hz, 1H).

Step B: 2-Isopropyl-2-(α-Hydroxybutyl)-1,3-Dithiane (41)

To a solution of (39) (4 g, 24.7 mmol) in anhydrous tetrahydrofuran (50 mL) at −20° C. was dropwise added n-butyl lithium (1.6M in hexane, 18.5 mL, 29.6 mmol). The stirred mixture was allowed to warm room temperature over 4 h and then cooled to −20° C. again. To this solution was added slowly a solution of n-butyraldehyde (2.7 mL, 29.6 mmol) in anhydrous tetrahydrofuran (10 mL). The resulting mixture was stirred for 16 h between −20° C. and room temperature. The reaction was quenched with saturated ammonium chloride solution and the mixture extracted with ethyl acetate. The organic layer was separated and dried over $Na_2SO_4$. After removing the solvent under reduced pressure, flash column chromatography of the residue on silica gel, eluting with 5% ethyl acetate/hexane provided 5 g (85%) of the title compound as a yellow oil. $^1$H NMR ($CDCl_3$, 400 MHz): δ 0.96 (t, J=7.2 Hz, 3H), 1.11 (d, J=6.8, Hz, 3H), 1.17 (d, J=6.8 Hz, 3H), 1.42-1.52 (m, 2H), 1.76 (m, 1H), 1.87-1.95 (m, 2H), 2.04 (m, 2H), 2.62 (m, 4H), 2.94 (m, 2H), 4.03 (d, J=5.2 Hz, 1H).

Step C: 4-Hydroxy-2-Methylheptan-3-one (43)

To a solution of (41) (5.0 g, 21.4 mmol) in acetonitrile (270 mL) was added under vigorous stirring a solution of $Hg(ClO_4)_2$ in methanol (30 mL). The resulting mixture was stirred at room temperature for 2 h. After filtration, the filtrate was carefully concentrated under reduced pressure without heating. Purification of the residue using silica gel flash column chromatography (10% ethyl acetate/hexane) provided 2.8 g (91%) of the title compound as colorless liquid. $^1$H NMR ($CDCl_3$, 400 MHz): δ 0.91 (t, J=7.2 Hz, 3H), 1.09 (d, J=7.2 Hz, 3H), 1.10 (d, J=7.2 Hz, 3H), 1.35-1.46 (m, 4H), 1.75 (m, 1H), 2.80 (m, 1H), 3.45 (d, J=5.2 Hz, 1H), 4.29 (m, 1H).

Step D: 2-Methylheptan-3-one-4-p-Nitrophenyl Carbonate (45)

To a mixture of (43) (1.1 g, 7.6 mmol), p-nitrophenyl chloroformate (1.84 g, 9.2 mmol) in anhydrous dichloromethane at 0° C. was added slowly a solution of 4-dimethylaminopyridine (1.12 g, 9.2 mmol) in dichloromethane. After stirring for 1 h at 0° C. and for 4 h at room temperature, the reaction was quenched with 10% citric acid. The organic phase was separated, dried over $Na_2SO_4$, and concentrated in vacuo. Flash column chromatography of the residue, eluting with 30% dichloromethane/hexane, provided 2 g (85%) of the title compound as an off-white solid. $^1$H NMR ($CDCl_3$, 400 MHz): δ 0.99 (t, J=7.6 Hz, 3H), 1.12 (d, J=6.8 Hz, 3H), 1.18 (d, J=6.8 Hz, 3H), 1.51 (m, 2H), 1.84 (m, 2H), 2.82 (m, 1H), 5.17 (m, 1H), 7.42 (d, J=6.8 Hz, 2H), 8.25 (d, J=6.8 Hz, 2H).

Step E: 1-{[(α-Isobutanoylbutoxy)carbonyl]aminomethyl}-1-Cyclohexane Acetic Acid (47)

To a mixture containing gabapentin (820 mg, 4.8 mmol) and triethylamine (1.35 mL, 9.6 mmol) in dichloromethane (20 mL) was added trimethylchlorosilane (1.22 mL, 9.6 mmol) and the resulting mixture was stirred for 20 min. To this solution was added (45) (1 g, 3.2 mmol) in dichloromethane (10 mL) and the resulting mixture was stirred for 60 min. The reaction mixture was washed with 10% citric acid (20 mL) and the organic layer separated. The aqueous layer was further extracted with ether (3×10 mL) and the combined organic extracts were dried over $MgSO_4$ then concentrated in vacuo. Chromatography of the residue on silica gel, eluting with hexane: ethyl acetate (4:1) to remove p-nitrophenol, then further eluting with hexane:ethyl acetate (1:4) gave 780 mg (72%) of the title compound. $^1$H NMR ($CDCl_3$, 400 MHz): δ 0.91 (t, J=7.2 Hz, 3H), 1.04 (d, J=6.8 Hz, 3H), 1.12 (d, J=6.8 Hz, 3H), 1.36-1.53 (m, 12H), 1.74 (m, 2H), 2.33 (s, 2H), 2.78 (m, 1H), 3.22 (m, 2H), 5.11 (m, 1H), 5.48 (t, 1H, NH). MS (ESI) m/z 342.24 (M+H$^+$).

Step F: 1-{[(α-Isobutanoyloxybutoxy)carbonyl]aminomethyl}-1-Cyclohexane Acetic Acid (37)

To a solution of (47) (780 mg, 2.3 mmol) in dichloromethane (20 mL) was added m-chloroperoxybenzoic acid (1.03 g, 4.6 mmol) and $NaHCO_3$ (386 mg, 4.6 mmol). After stirring for 16 h at room temperature, another batch of m-chloroperoxybenzoic acid (791 mg, 4.6 mmol) and $NaHCO_3$ (386 mg, 4.6 mmol) was added. The resulting mixture was stirred for another 8 h and then treated with 10% citric acid. After filtration, the organic layer was separated, dried over $Na_2SO_4$, and concentrated. The residue was purified by reverse phase preparative HPLC to afford 79 mg (11%) of the title compound. $^1$H NMR ($CDCl_3$, 400 MHz): δ 0.94 (t, J=7.2 Hz, 3H), 1.153 (d, J=7.2 Hz, 3H), 1.150 (d, J=7.2 Hz, 3H), 1.32-1.58 (m, 12H), 1.74 (m, 2H), 2.28 (s, 2H), 2.56 (m, 1H), 3.23 (m, 2H), 5.27 (t, J=6.8 Hz, 1H, NH), 6.71 (t, J=5.6 Hz, 1H). MS (ESI) m/z 358.30 (M+H$^+$).

5.11 Example 11

α-(Benzoyloxy)benzyl-N-2-Phenethyl Carbamate (49)

Step A: (2-Oxo-1,2-Diphenylethyl)-N-2-Phenethyl Carbamate (51)

A solution of benzoin (2.0 g, 9.42 mmol) and phenethylisocyanate (4.16 g, 28.27 mmol) in toluene (60 mL) was refluxed overnight. After removing the solvent under reduced pressure, the residue was purified by flash chromatography on silica gel (30% ethyl acetate in hexane) to afford 3.0 g (89%) the title compound. $^1$H NMR ($CDCl_3$): δ 7.95 (2H, dd, J=8.4, 1.2 Hz); 7.50-7.17 (8H, m); 6.86 (1H, s); 5.08 (1H, t, J=7.2 Hz); 3.45 (2H, q. J=7.2 Hz); 2.81 (2H, t, J=7.2 Hz).

Step B: α-(Benzoyloxy)benzyl-N-2-Phenethyl Carbamate (49)

$Na_2CO_3$ (165 mg, 1.56 mmol) and mCPBA (349 mg, 1.56 mmol) was added to a stirred, 0° C. solution of (51) (280 mg (0.78 mmol) in dichloromethane (10 mL). The reaction mixture was allowed to warm to room temperature and stirred for 24 hours. The reaction mixture was then diluted with $CH_2Cl_2$, washed with 10% aqueous $Na_2CO_3$ solution, brine and dried over $Na_2SO_4$. The solvent was removed in vacuo and the residue was purified by flash chromatography on silica gel (20% ethyl acetate in hexane) to afford 165 mg (45%) of the title compound. $^1$H NMR ($CDCl_3$): δ 8.10 (2H, dd, J=8.4, 1.2 Hz); 7.94 (1H, s); 7.60-7.17 (8H, m); 4.89 (1H, br s); 3.49 (2H, t, J=7.2 Hz); 2.84 (2H, t, J=7.2 Hz).

5.12 Example 12

1-(Acetoxy)ethyl-N-2-Phenethyl Carbamate (53)

Step A: (1-Methyl-2-Oxo-Propyl) N-2-Phenethyl Carbamate (55)

A solution of 3-hydroxy-2-butanone (440 mg, 5 mmol) and phenethylisocyanate (810 mg, 5.5 mmol) in toluene was stirred for two days at 50° C. and the solvent was then removed under reduced pressure. The residue was purified by flash chromatography on silica gel (25% ethyl acetate in hexane) to afford 305 mg (26%) of the title compound. $^1$H NMR ($CDCl_3$): δ 7.31-7.19 (5H, m); 5.02 (1H, q, J=6.4 Hz);

4.89 (1H, br s); 3.47 (2H, t, J=6.4 Hz); 2.83 (2H, t, J=6.4 Hz); 2.15 (3H, s); 1.35 (3H, d, J=6.4 Hz).

Step B: 1-(Acetoxy)ethyl-N-2-Phenethyl Carbamate (53)

mCPBA (77%, 580 mg, 2.60 mmol) was added to a stirred suspension of (55) (305 mg, 1.29 mmol)) and Na$_2$CO$_3$ (137.6 mg, 1.29 mmol) in dichloromethane (15 mL). The reaction mixture was stirred at room temperature for 48 hours, diluted with dichloromethane, washed with 10% Na$_2$CO$_3$ and brine and dried over Na$_2$SO$_4$. Solvent was removed under reduced pressure and the residue was purified by flash chromatography on silica gel (20% ethyl acetate in hexanes) to afford 202 mg (62%) of the title compound. $^1$H NMR (CDCl$_3$): δ 7.34-7.20 (5H, m); 6.82 (1H, q, J=5.2 Hz); 4.80 (1H, br s); 3.44 (2H, t, J=6.8 Hz); 2.82 (2H, t, J=6.8 Hz); 2.05 (3H,s); 1.44 (3H, d, J=5.2 Hz).

5.13 Example 13

1-Acetoxy-1-Methylethyl-2-N-Phenethyl Carbamate (57)

Step A: (1,1-Dimethyl-2-Oxo-Propyl) 2-N-Phenethyl Carbamate (59)

A solution of 3-hydroxy-3-methyl-2-butanone (510 mg, 5 mmol) and phenethylisocyanate (809 mg, 5.5 mmol) in toluene was stirred for three days at 50° C. and then concentrated in vacuo. The residue was purified by flash chromatography on silica gel (25% ethyl acetate in hexanes) to give 218 mg (17.5%) of the title compound. $^1$H NMR (CDCl$_3$): δ 7.33-7.20 (5H, m); 4.85 (1H, br s, 1H); 3.44 (2H, t, J=6.8 Hz); 2.82 (2H, t, J=6.8 Hz); 2.12 (3H, s); 1.43 (6H, s).

Step B: 1-Acetoxy-1-Methylethyl-2-N-Phenethyl Carbamate (57)

mCPBA (77%, 245 mg, 1.09 mmol) was added to a stirred suspension of (59) (109 mg, 0.44 mmol) and Na$_2$CO$_3$ (46 mg, 0.44 mmol) in dichloromethane (15 mL). The reaction mixture was stirred for 48 hours at room temperature and another batch of mCPBA (247 mg, 1.09 mmol) was added. After stirring for 3 more days, the reaction mixture was diluted with dichloromethane, washed with 10% Na$_2$CO$_3$ and brine and dried over Na$_2$SO$_4$. After concentration in vacuo, the residue was purified by flash chromatography on silica gel (20% ethyl acetate in hexanes) to afford 50 mg (43%) of (57). $^1$H NMR (CDCl$_3$): δ 7.34-7.19 (5H, m); 4.86 (1H, br. s, 1H); 3.43 (2H, t, J=6.7 Hz); 2.83 (2H, t, J =6.7 Hz). 2.09 (3H, s); 1.44 (6H, s).

5.14 Example 14

Benzaldehyde Dibenzoylacetal (61)

32% peracetic acid (0.67 mL, 3.79 mmol) was added to a suspension of desyl benzoate (300 mg, 0.95 mmol) and Na$_2$CO$_3$ (402 mg, 3.79 mmol) in dichloromethane (5 mL) at 0° C. The reaction mixture was stirred overnight at room temperature, diluted with dichloromethane, washed with saturated NaHCO$_3$ and brine and dried over Na$_2$SO$_4$. Concentration in vacuo provided 250 mg the title compound (79%). $^1$H NMR (CDCl$_3$): δ 8.22 (1H, s); 7.73-7.71 (2H, m); 7.59-7.55 (2H, m); 7.48-7.42 (7H, m).

5.15 Example 15

Ethyl α-Benzoyloxybenzyl Methylphosphonate (63)

Step A: Ethyl α-Benzoylbenzyl Methylphosphonate (65)

A solution of ethyl methyl phosphonate (1.81 mmol), diisopropylethylamine (2.71 mmol) and desyl bromide (1.81 mmol) in DMF was stirred overnight at 70° C. The reaction mixture was cooled to room temperature, diluted with ether, washed with water, citric acid and brine and the organic phase was dried over Na$_2$SO$_4$. After concentration in vacuo, the crude product was purified by flash chromatography (2% methanol in dichloromethane) to afford 650 mg (54.2%) of ethyl α-benzoylbenzyl methyl phosphonate (65) as four diasteroisomers. $^1$H NMR (CDCl$_3$): δ 7.95-7.90 (2H, m); 7.51-7.35 (8H, m); 6.74 (1H, m); 4.19-3.70 (2H, m); 1.64 (1.5H, d, J18.0); 1.34 (1.5H, d, J=18 Hz); 1.25 (1.5H, t, J=7.2 Hz); 1.17 (1.5H, t, J=7.2Hz).

Step B: Ethyl α-Benzoyloxybenzyl Methylphosphonate (63)

A suspension of ethyl α-benzoylbenzyl methyl phosphonate (275 mg, 0.87 mmol) (65), mCPBA (77%, 388 mg, 1.73 mmol) and Na$_2$CO$_3$ (183 mg, 1.73 mmol) in 5 mL of dichloromethane was stirred overnight at room temperature, diluted with dichloromethane, washed with saturated NaHCO$_3$ and brine and dried over Na$_2$SO$_4$. Concentration in vacuo followed by purification of the residue by flash chromatography on silica gel, eluting with 15% ethyl acetate in hexane, afforded 200 mg (69%) of ethyl α-benzoyloxybenzyl methyl phosphonate (37). $^1$H NMR (CDCl$_3$): 8.11-8.09 (2H, m); 7.68-7.42 (9H, m); 4.22-3.70 (2H, m); 1.62 (1.5H, d, J=18.4 Hz); 1.49 (1.5 H, d, J=18.0); 1.25 (1.5H, t, J=7.2 Hz); 1.17 (1.5H, t, J=7.2 Hz).

5.16 Example 16

1-{[(α-(S)-Isobutanoyloxyisobutoxy)carbonyl]aminomethyl}-1-Cyclohexane Acetic Acid (181) and 1-{[(α-(R)-Isobutanoyloxyisobutoxy)carbonyl]aminomethyl}-1-Cyclohexane Acetic Acid (183)

Step A: (S)- and (R)-N-(2-Hydroxy-3-Methylbutyroyl)morpholine (161) and (163)

To a stirred solution of (R)- or (S)-2-hydroxy-3-methylbutyric acid (0.1 mol) and N-hydroxysucciniimide (0.12 mol) in dichloromethane (200 mL) at ice-bath temperature under nitrogen atmosphere was added dropwise a solution of dicyclohexylcarbodiimide (0.12 mol) in dichloromethane (100 mL). After stirring at room temperature for 3 h, the reaction mixture was filtered and the precipitate was washed with dichloromethane (2×25mL). The combined filtrate was cooled in an ice-bath and then was added dropwise a solution of morpholine (0.22 mol) in dichloromethane (50 mL). The resulting mixture was stirred at ice-bath temperature for 1 h and then overnight at room temperature. The reaction mixture was filtered, and the precipitate was washed with dichloromethane (2×25mL). The combined filtrate was washed successively with water (100 mL), 2% HCl solution (100 mL), brine (100 mL) and dried over anhydrous sodium sulfate.

After removing the solvent under reduced pressure, the residue was purified by passing through a short silica gel column using ethyl acetate as eluent to afford the title compounds in 84-97% yield as viscous liquids. $^1$H NMR (CDCl$_3$, 400 MHz): δ 0.80 (3H, d), 1.05 (3H, d), 1.76-1.84 (1H, m), 3.41 (2H, br. t), 3.54 (1H, br. s, OH), 3.62-3.71 (6H, m), 4.21 (1H, br. s). MS (ESI) m/z 188.26 (M+H$^+$).

Step B: (S)- and (R)-N-(2-Benzyloxy-3-Methylbutyroyl)morpholine (165) and (167)

To a stirred suspension of sodium hydride (0.09 mol) in anhydrous dimethylformamide (25 mL) under nitrogen atmosphere at 0° C. was added dropwise a solution of the appropriate α-hydroxyacid amide 161 or 163 (0.75 mol) in dimethylfornamide (50 mL). After stirring for 30 min, a solution of benzyl bromide (0.10 mol) in dimethylformamide (25 mL) was added dropwise into the reaction mixture at 0° C. The resulting mixture was stirred at 0° C. for 1 h and then, at room temperature for 5-8 h (monitored by TLC). The mixture was poured onto crushed ice and acidified (to pH~6) with 5% HCl solution. The mixture was extracted with dichloromethane (4×50 mL). The combined extract was washed with water (2×50 mL), dried over anhydrous sodium sulfate and then, evaporated under reduced pressure. The residue was purified through a short silica gel column eluting with 50-100% ethyl acetate and hexane to afford the title compounds in 85-90% yield as colorless viscous liquids. $^1$H NMR (CDCl$_3$, 400 MHz): 6 0.93 (3H, d), 1.06 (3H, d), 1.95-2.02 (1H, m), 3.56 (2H, br. t), 3.64-3.67 (6H, m), 3.78 (1H, d), 4.45 (1H, d), 4.63 (1H, d), 7.31 (5H, m). MS (ESI) m/z 278.29 (M+H$^+$).

Step C: (S)- and (R)-2,5-Dimethyl-4-Benzyloxy-Hexan-3-one (169) and (171)

To a stirred solution of compound 165 or 167 (0.05 mol) in anhydrous tetrahydrofuran (150 mL) under nitrogen atmosphere at –78 ° C. was added dropwise a solution of isopropyl lithium (0.075 mol). After stirring at –78 ° C. for 1-3 h (monitored by TLC), the reaction mixture was poured into ice-cold saturated ammonium chloride solution (100 mL). The mixture was extracted with ethyl acetate (4×50 mL), washed with brine (50 mL), dried over anhydrous sodium sulfate and concentrated under reduced pressure. The residue was purified by passing through a short silica gel column using a gradient of 0-25% ethyl acetate/hexane as eluent to afford the title compounds in 79-95 yield as colorless viscous liquids. $^1$H NMR (CDCl$_3$, 400 MHz): δ 0.95 (6H, br. d), 1.05 (3H, br. d), 1.07 (3H, br. d), 2.03-2.11 (1H, m), 2.92-2.99 (1H, m), 3.66 (1H, br. d), 4.33 (1H, br. d), 4.62 (1H, br. d), 7.34 (3H, m), 7.35 (2H, m). MS (ESI) m/z 235.16 (M+H$^+$).

Step D: (S)- and (R)-2,5-Dimethyl-4-Hydroxy-Hexan-3-one (173) and (175)

To a solution of compound 169 or 171 (0.03 mol) in 20 mL of methanol was added 10% Pd-C (50% w/w) under nitrogen atmosphere. The resulting mixture was agitated with a stream of hydrogen (50 psi) at room temperature for 24 hrs (monitored by TLC). The reaction mixture was filtered through a Celite® pad, and the precipitate washed with methanol (3×25 mL). The combined filtrate was concentrated under reduced pressure at cold water bath temperature (<20° C.). The residue was passed through a short silica gel column using a gradient of 0-25% diethylether and n-pentane as eluents to afford the title compounds in 89-98% yield as colorless liquids. The enantiomeric excess of these chiral hydroxyketones was determined from the $^1$H NMR spectral data of their Mosher ester derivatives (prepared as in Step E below). $^1$H NMR (CDCl$_3$, 400 MHz): δ 0.69 (3H, br. d), 1.10 (3H, br. d), 1.11 (3H, br. d), 1.13 (3H, br. d), 2.12-2.19 (1H, m), 2.81 (1H, br. hept), 3.37 (1H, br. d, OH), 4.29 (1H, br. d). MS (ESI) m/z 145.12 (M+H$^+$).

Step E: Synthesis of Mosher Esters of (173) and (175)

To a stirred solution containing the appropriate α-hydroxyketone. (0.1 mmol), triethylamine (0.12 mmol) and DMAP (0.04 mmol) in anhydrous dichloromethane under nitrogen atmosphere at 0° C. was added a solution of (S)-(+)-Mosher acid chloride (0.12 mmol) in dichloromethane (1 mL). The resulting mixture was stirred at 0° C. for 2 h and then, at room temperature for 4-6 h (monitored by TLC). The reaction mixture was poured into ice-cold water (15 mL) and extracted with dichloromethane (3×15 mL). The combined extract was washed successively with 10% aqueous NaHCO$_3$ solution (15 mL) and brine (15 mL). The organic layer was separated, dried over anhydrous sodium sulfate and concentrated under reduced pressure. The residue was quickly passed through a short silica gel column using 50% diethyl ether and hexane as eluents to remove the DMAP and the organic salts thereof as polar impurities in the crude reaction mixture. The diastereomeric excess of the Mosher esters was determined from the $^1$H NMR spectral data to be>90% for each isomer.

Mosher Ester of (173)

Colorless viscous liquid (de=>90%). $^1$H NMR (CDCl$_3$, 400 MHz): δ 0.85 (3H, d), 1.06 (3H, d), 1.10 (3H, d), 1.19 (3H, d), 2.32-2.39 (1H, m), 2.77 (1H, hpt.), 3.57 (3H, s), 5.23 (1H, d), 7.42 (3H, m), 7.59 (2H, m).

Mosher Ester of (175)

Colorless viscous liquid ((de=>90%). $^1$H NMR (CDCl$_3$, 400 MHz): δ 0.83 (3H, d), 0.96 (3H, d), 1.09 (3H, d), 1.22 (3H, d), 2.26-2.34 (1H, m), 2.79 (1H, hpt.), 3.62 (3H, s), 5.21, (1H, d), 7.42 (3H, m), 7.71 (2H, m).

Step F: 1-{[(α-(S)-Isobutanoylisobutoxy)carbonyl]aminomethyl}-1-Cyclohexane Acetic Acid (177) and 1-{[(α-(R)-Isobutanoylisobutoxy)carbonyl]aminomethyl}-1-Cyclohexane Acetic Acid (179)

To a stirred solution of α-hydroxyketone 173 or 175 (1g, 7 mmol) and DMAP (1g, 9 mmol) in anhydrous dichloromethane (25 mL) under nitrogen atmosphere at 0° C. was added dropwise a solution of p-nitrophenylchloroformate in dichloromethane (25 mL). The resulting mixture was stirred for 5-6 h (monitored by TLC) and then poured into 10% aqueous NaHCO$_3$ solution and extracted with dichloromethane (2×25 mL). The combined. extract was washed with brine (25 mL), dried over anhydrous sodium sulfate and concentrated under reduced pressure to afford the corresponding carbonate derivative in nearly quantitative yield.

In a separate flask, gabapentin (1.71 g, 10 mmol) was treated with chlorotrimethylsilane (3.16 g, 21 mmol) in dichloromethane (100 mL) in the presence triethylamine (2.22 g, 22 mmol) at 0° C. for 30 min. To this reaction mixture, a solution of the appropriate carbonate described above in dichloromethane (25 mL) was added at 0° C. followed by pyridine (0.79 g, 10 mmol). The resulting mixture was stirred at 0° C. for 3 h and then at room temperature for 12-15 h (monitored by LC/MS). The reaction mixture was poured into cold water and extracted with dichloromethane (3×50 mL). The combined extract was washed successively with 2% aqueous HCl solution (50 mL), brine (2×50 mL) and dried over anhydrous sodium sulfate. After evaporating the solvent under reduced pressure the residue was purified by preparative LC/MS to afford the title compounds in 35-48% yield as colorless viscous liquids. $^1$H NMR (CDCl$_3$, 400 MHz): δ 0.86 (3H, d), 1.04 (6H, m), 1.13 (3H, d), 1.35-1.54 (10H, m), 2.21-2.26 (H, m), 2.33 (2H, d), 2.78 (1H, hpt.), 3.22 (2H, br. t), 5.04 (1H, d), 5.43 (1H, br. t, NH). MS (ESI) m/z 342.42 (M+H$^+$).

Step G: 1-{[(α-(S)-Isobutanoyloxyisobutoxy)carbonyl]aminomethyl}-1-Cyclohexane Acetic Acid (181) and 1-{[(α-(R)-Isobutanoyloxyisobutoxy)carbonyl]aminomethyl}-1-Cyclohexane Acetic Acid (183)

To a stirred suspension of m-chloroperoxybenzoic acid (1.55 g, 9 mmol) and sodium hydrogen-phosphate (1.71 g, 9 mmol) in dichloromethane (50 mL) at room temperature was added a solution of compound 177 or 179 (1g, 3 mmol) in dichloromethane (50 mL). The resulting mixture was stirred at room temperature for 48 h (monitored by LC/MS) and then poured into cold water (100 mL) and acidified (to pH~5) with 5% aqueous HCl solution. The mixture was extracted with ethyl acetate (4×50 mL). The combined organic extract was washed with brine (50 mL), dried over anhydrous sodium sulfate and concentrated under reduced pressure. The residue was purified by preparative LC/MS technique to afford the title compounds as colorless viscous liquids in 4-10% yield. $^1$H NMR (CDCl$_3$, 400 MHz): δ 0.94 (6H, d), 1.14 (3H, d), 1.15 (3H, d), 1.38-1.50 (10H, m), 1.99 (1H, m), 2.30 (2H, s), 2.53 (1H, hpt), 3.22 (2H, br. t), 5.29 (1H, br. t, NH), 6.11 (1H, br. s). $^1$H NMR (CD$_3$OD, 400 MHz): 0.95 (d, J=7.2 Hz, 3H), 0.97 (d, J=7.2 Hz, 3H), 1.05 (d, 3H), 1.06 (d, 3H), 1.32-1.58 (m, 10H), 1.98 (m, 1H), 2.24 (s, 2H), 2.45 (m, 1H), 3.24 (m, 2H), 6.42 (d, 1H). MS (ESI) m/z 356.28 (M–H)$^-$.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims.

All publications and patents cited herein are incorporated by reference in their entirety.

What is claimed is:

1. A compound of structural Formula (X):

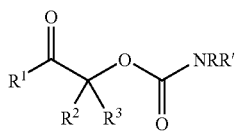

(X)

or a pharmaceutically acceptable salt thereof, wherein:
—NRR' is acebutalol, albuterol, alprenolol, atenolol, bunolol, bupropion, butopamine, butoxamine, carbuterol, cartelolol, colterol, deterenol, dexpropanolol, diacetolol, dobutamine, exaprolol, oxprenolol, fenoterol, fenyripol, labotolol, levobunolol, metolol, metaproterenol, metoprolol, nadolol, pamatolol, penbutolol, pindolol, pirbuterol, practolol, prenalterol, primidolol, prizidilol, procaterol, propanolol, quinterenol, rimiterol, ritodrine, soterenol, sulfinalol, sulfonterol, suloctidil, terbutaline, timolol, tiprenolol, thiabendazole, albendazole, albutoin, alendronate, alinidine, alizapride, amiloride, aminorex, aprinocid, cambendazole, cimetidine, cisapride, clonidine, delavirdine, etintidine, fenbendazole, fenmetazole, flubendazole, fludorex, gabapentin, incadronate, lobendazole, mebendazole, metazoline, metoclopramide, methylphenidate, mexiletine, neridronate, nocodazole, oxfendazole, oxibendazole, oxmetidine, parbendazole, pramipexole, prazosin, pregabalin, procainamide, ranitidine, tetrahydrazoline, tiamenidine, tinazoline, tiotidine, tocainide, tolazoline, tramazoline, xylometazoline, dimethoxyphenethylamine, N-[3(R)-[2-piperidin-4-ylethyl]-2-piperidone-1-yl]acetyl-3(R)-methyl-β-alanine, adrenolone, amidephrine, amphetamine, aspartame, bamethan, betahistine, carbidopa, clorprenaline, chlortermine, dopamine, levodopa (L-Dopa), epinephrine, etryptamine, fenfluramine, methyldopamine, norepinephrine, enviroxime, nifedipine, nimodipine, triamterene, pipemidic acid, 1-ethyl-6-fluoro-1,4dihydro-4-oxo-7-(1-piperazinyl)-1,8-napthyridine-3-carboxylic acid, 1-cyclopropyl-6-fluoro-1,4-dihydro-4-oxo-7-(piperazinyl)-3-quinolinecarboxylic acid, amifostine, baclofen, clonidine, ciprofloxacin, daunorubicin, doxorubicin, gentamycin, kanamycin, meropenem, neomycin, tobramycin, trovafloxacin or vigabatrin; wherein a hydrogen atom of a primary or secondary amine group is replaced with a covalent bond;
R$^1$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, and
R$^2$ and R$^3$ are independently hydrogen, alkyl, substituted alkyl, alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, heteroarylalkyl or substituted heteroarylalkyl or optionally, R$^2$ and R$^3$ together with the atom to which they are attached form a cycloalkyl, substituted cycloalkyl, cycloheteroalkyl or substituted cycloheteroalkyl ring;
wherein each substituent is independently selected from the group consisting of —X, —R$^{14}$, =O, —OR$^{14}$, —SR$^{14}$, —NR$^{14}$R$^{15}$, —CF$_3$, —CN, —NO$_2$, —C(O)R$^{14}$, —C(O)OR$^{14}$, and —C(O)NR$^{14}$R$^{15}$, where each X is independently a halogen; and each R$^{14}$, and R$^{15}$ is independently hydrogen or C$_{1-10}$ alkyl.

2. The compound or pharmaceutically acceptable salt of claim 1, wherein:
R$^1$ is selected from the group consisting of hydrogen, alkyl, substituted alkyl, aryl, substituted aryl, arylalkyl, cycloalkyl, cycloheteroalkyl, heteroaryl, substituted heteroaryl; and
R$^2$ and R$^3$ are independently hydrogen, alkyl, alkoxycarbonyl, aryl, arylalkyl, carbamoyl, cycloalkoxycarbonyl or heteroaryl.

3. The compound or pharmaceutically acceptable salt of claim 2, wherein:
R$^1$ is selected from the group consisting of methyl, ethyl, propyl, isopropyl, butyl, isobutyl, sec-butyl, tert-butyl, pentyl, isopentyl, sec-pentyl, neopentyl, cyclobutyl, cyclopentyl, cyclohexyl, phenyl, 4-methoxyphenyl, benzyl, phenethyl, styryl or 3-pyridyl; and
R$^2$ and R$^3$ are independently selected from the group consisting of hydrogen, methyl, ethyl, propyl, isopropyl, butyl, isobutyl, sec-butyl, tert-butyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, cyclohexyloxycarbonyl, phenyl, benzyl, phenethyl or 3-pyridyl.

4. The compound or pharmaceutically acceptable salt of claim 3, wherein:
$R^1$ is selected from the group consisting of methyl, ethyl, propyl, isopropyl, butyl, isobutyl, sec-butyl, tert-butyl, pentyl, isopentyl, sec-pentyl, neopentyl, cyclobutyl, cyclopentyl, cyclohexyl, phenyl, 4-methoxyphenyl, benzyl, phenethyl, styryl or 3-pyridyl; and
$R^2$ is selected from the group consisting of hydrogen, methyl, ethyl, propyl, isopropyl, butyl, isobutyl, sec-butyl, tert-butyl, phenyl, benzyl, phenethyl or 3-pyridyl, and $R^3$ is hydrogen.

5. The compound or pharmaceutically acceptable salt of claim 3, wherein:
$R^1$ is selected from the group consisting of methyl, ethyl, propyl, isopropyl, butyl, isobutyl, sec-butyl, tert-butyl, pentyl, isopentyl, sec-pentyl, neopentyl, cyclobutyl, cyclopentyl, cyclohexyl, phenyl, 4-methoxyphenyl, benzyl, phenethyl, styryl or 3-pyridyl; and
$R^2$ is selected from the group consisting of methyl, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and cyclohexyloxycarbonyl, and $R^3$ is methyl.

6. The compound or pharmaceutically acceptable salt of claim 1, wherein —NRR' is amifostine, baclofen, carbidopa, clonidine, ciprofloxacin, cisapride, daunorubicin, doxorubicin, fenoterol, gabapentin, gentamycin, kanamycin, levodopa, meropenem, metazoline, neomycin, pregabalin, tobramycin, trovafloxacin or vigabatrin wherein a hydrogen atom of a primary or secondary amine group is replaced with a covalent bond.

7. A pharmaceutical composition comprising the compound or pharmaceutically acceptable salt of claim 1 and a pharmaceutically acceptable vehicle.

8. A compound of formula (IV):

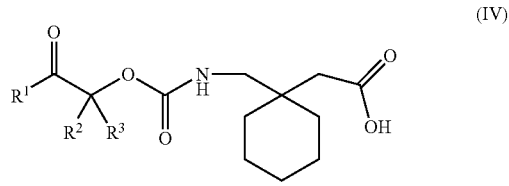

(IV)

or a pharmaceutically acceptable salt thereof, wherein:
$R^1$ is selected from the group consisting of methyl, ethyl, propyl, isopropyl, butyl, isobutyl, sec-butyl, tert-butyl, phenyl, benzyl, and 3-pyridyl;
$R^2$ is selected from the group consisting of hydrogen, methyl, ethyl, propyl, isopropyl, butyl, isobutyl, sec-butyl, tert-butyl, and phenyl; and
$R^3$ is hydrogen.

9. The compound or pharmaceutically acceptable salt of claim 8 wherein $R^2$ is methyl.

10. The compound or pharmaceutically acceptable salt of any one of claims 1 and 2, wherein each substituent is independently selected from the group consisting of —X, —$R^{14}$, —$OR^{14}$, —$NR^{14}R^{15}$, —$CF_3$, —CN, —$NO_2$, —$C(O)R^{14}$, —$C(O)OR^{14}$, and —$C(O)NR^{14}R^{15}$, where each X is independently a halogen; and each $R^{14}$ and $R^{15}$ is independently hydrogen or $C_{1-10}$ alkyl.

* * * * *